(12) United States Patent
Mazar et al.

(10) Patent No.: US 12,741,039 B2
(45) Date of Patent: Sep. 22, 2026

(54) UROKINASE PLASMINOGEN ACTIVATOR RECEPTOR-TARGETED RADIOPHARMACEUTICAL

(71) Applicants: Northstar Medical Technologies, LLC, Beloit, WI (US); Monopar Therapeutics Inc, Wilmette, IL (US)

(72) Inventors: Andrew Mazar, Lake Forest, IL (US); James T. Harvey, Naperville, IL (US); R. Keith Frank, Lake Jackson, TX (US); Jaime Simon, Angleton, TX (US); Jason Rogers, Lake Jackson, TX (US)

(73) Assignees: NORTHSTAR MEDICAL TECHNOLOGIES, LLC, Beloit, WI (US); MONOPAR THERAPEUTICS INC., Wilmette, IL (US)

( * ) Notice: Subject to any disclaimer, the term of this patent is extended or adjusted under 35 U.S.C. 154(b) by 1132 days.

(21) Appl. No.: 17/749,763

(22) Filed: May 20, 2022

(65) Prior Publication Data

US 2022/0409751 A1 Dec. 29, 2022

Related U.S. Application Data

(60) Provisional application No. 63/191,506, filed on May 21, 2021, provisional application No. 63/191,499, filed on May 21, 2021.

(51) Int. Cl.

*A61K 51/04* (2006.01)
*A61K 51/10* (2006.01)
*A61K 51/12* (2006.01)

(52) U.S. Cl.

CPC ........ *A61K 51/1096* (2013.01); *A61K 51/044* (2013.01); *A61K 51/0482* (2013.01);

(Continued)

(58) Field of Classification Search

None

See application file for complete search history.

(56) References Cited

U.S. PATENT DOCUMENTS 5,766,886 A 6/1998 Studnicka et al.
5,770,196 A 6/1998 Studnicka (Continued)

FOREIGN PATENT DOCUMENTS

WO 9311794 A1 6/1993
WO 2011011592 A1 1/2011
WO 2021257552 A1 12/2021

OTHER PUBLICATIONS

Jensen et al., Chin Med J (Engl). Apr. 21, 2025;138(10):1153-1162 (Year: 2025).*

(Continued)

*Primary Examiner* — Karl J Puttlitz

(74) *Attorney, Agent, or Firm* — MARSHALL, GERSTEIN & BORUN LLP

(57) ABSTRACT

A targeted radiopharmaceutical of chemical Formula I, below, is disclosed wherein $Q^{+3}$ is a (Continued)

I

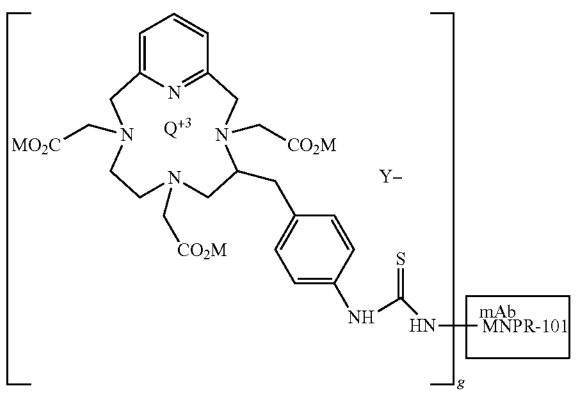

trivalent radioactive isotope ion; M is a proton (H+), an ammonium ion or an alkali metal ion; "g" is a number that is 1 to about 12; the boxed mAb MNPR-101 represents the chemically-bonded humanized mAb MNPR-101; and Y− is an optional anion present in an amount needed to balance the ionic charge. A pharmaceutical composition that comprises a theranostic effective amount of a Formula I targeted radiopharmaceutical dissolved or dispersed in a pharmaceutically acceptable diluent is also disclosed, as are a method for treating and/or diagnosing a mammalian host having a disease, disorder or condition characterized by undesired angiogenesis, tumor growth and/or tumor metastasis. A targeted pro-radiopharmaceutical construct similar to that of Formula I but without the radioisotope (Formula III) is also contemplated.

26 Claims, 1 Drawing Sheet

Specification includes a Sequence Listing.

(52) U.S. Cl.
CPC ...... *A61K 51/1054* (2013.01); *A61K 51/1093* (2013.01); *A61K 51/121* (2013.01); *A61K 2121/00* (2013.01)

(56) References Cited

U.S. PATENT DOCUMENTS

| | | | |
|---|---|---|---|
| 5,821,123 | A | 10/1998 | Studnicka |
| 5,869,619 | A | 2/1999 | Studnicka |
| 8,101,726 | B2 | 1/2012 | Parry et al. |
| 2004/0067924 | A1 | 4/2004 | Frank et al. |
| 2008/0199476 | A1 | 8/2008 | Parry et al. |
| 2009/0180952 | A1 | 7/2009 | Parry et al. |
| 2019/0374660 | A1 | 12/2019 | Eder et al. |

OTHER PUBLICATIONS

La Mendola et al., Int J Mol Sci. Sep. 19, 2022;23(18):10962 (Year: 2022).*

Dudley et al., Angiogenesis. Apr. 15, 2023;26(3):313-347 (Year: 2023).*

International Search Report re application No. PCT/US22/30272, dated Oct. 5, 2022.

Written Opinion re application No. PCT/US22/30272, dated Oct. 5, 2022.

Cooper et al., Comparison of 64 Cu-complexing bifunctional chelators for radioimmunoconjugation: labeling efficiency, specific activity, and in vitro/in vivo stability, Biocon. Chem., 23(5): 1029-1039 (May 2012).

Novy et al., The effect of chelator type on in vitro receptor binding and stability in 177 Lu-labeled cetuximab and panitumumab, J. Labelled Comp. Radiopharma., 57(7): 448-452 (May 2014).

Poty, S. et al, "α-Emitters for Radiotherapy: From Basic Radiochemistry to Clinical Studies—Part 1," Journal of Nuclear Medicine Jun. 2018, 59 (6) 878-884; doi: https://doi.org/10.2967/jnumed.116.186338.

Pearson, R.G., "Hard and Soft Acids and Bases," Journal of the American Chemical Society, vol. 85, No. 22, pp. 3533-3539, Nov. 20, 1963.

Parr, R.G. et al, "Absolute Hardness: Companion Parameter to Absolute Electronegativity," Journal of the American Chemical Society, vol. 105, No. 26, pp. 7512-7516, Dec. 1, 1983.

Pearson, R.G., "Absolute Electronegativity and Hardness: Application to Inorganic Chemistry," Inorganic Chemistry, vol. 27, No. 4, pp. 734-740, Feb. 1, 1988.

Thiele, N.A. et al, "Actinium-225 for Targeted α Therapy: Coordination Chemistry and Current Chelation Approaches," Cancer Biotherapy and Radiopharmaceuticals, vol. 33, No. 8, 2018, pp. 336-348; doi: 10.1089/cbr.2018.2494.

Davis, I.A. et al, "Comparison of 225 Actinium Chelates: Tissue Distribution and Radiotoxicity," Nuclear Medicine and Biology, vol. 26, No. 5, Jul. 1999, pp. 581-589; https://doi.org/10.1016/S0969-8051(99)00024-4.

Robertson, A.K.H. et al, "Development of 225Ac Radiopharmaceuticals: TRIUMF Perspectives and Experiences," Curr Radiopharm 2018;11(3):156-172. doi: 10.2174/1874471011666180416161908.

McDevitt, M.R. et al, "Tumor Therapy with Targeted Atomic Nanogenerators," Science. Nov. 16, 2001;294 (5546):1537-40. doi: 10.1126/science.1064126. PMID: 11711678 (Abstract only).

McDevitt, M.R et al, "Design and Synthesis of 225Ac Radioimmunopharmaceuticals," Appl Radiat Isot. Dec. 2002;57 (6):841-7. doi: 10.1016/s0969-8043(02)00167-7. PMID: 12406626.

Maguire, W.F et al, "Efficient 1-Step Radiolabeling of Monoclonal Antibodies to High Specific Activity with 225Ac for α-Particle Radioimmunotherapy of Cancer," Journal of Nuclear Medicine, Sep. 2014, 55 (9) 1492-1498; doi: https://doi.org/10.2967/jnumed.114.138347.

Yapp, D.T.T. et al, "Imaging Tumor Vasculature Noninvasively with Positron Emission Tomography and RGD Peptides Labeled with Copper 64 Using the Bifunctonal Chelates DOTA, Oxo-DO3a. and PCTA," Molecular Imaging, Jun. 2013, 12(4):263-72; doi:10.2310/7290.2012.00044.

Park, S.I. et al, "Conventional and Pretargeted Radioimmunotherapy Using Bismuth-213 to Target and Treat non-Hodgkin Lymphomas Expressing CD20: A Preclinical Model Toward Optimal Consolidation Therapy to Eradicate Minimal Residual Disease," Blood (2010) 116 (20): 4231-4239, https://doi.org/10.1182/blood-2010-05-282327.

Yong, K. et al, "Application of 212Pb for Targeted α-particle Therapy (TAT): Pre-clinical and Mechanistic Understanding through to Clinical Translation," AIMS Medical Science, Review 2015, vol. 2, issue 3: 228-245. doi: 10.3934/medsci.2015.3.228.

Mulford, D.A. et al, "The Promise of Targeted α-Particle Therapy," Journal of Nuclear Medicine Jan. 2005, 46 (1 suppl) 199S-204S.

Bartos, B. et al, "Search of Ligands Suitable for 212Pb/212Bi in Vivo Generators," J Radioanal Nucl Chem. Sep. 19, 2013;295(1):205-209. doi: 10.1007/s10967-012-2238-4.

Saleem, A. et al, "Why Are We Failing to Implement Imaging Studies with Radiolabelled New Molecular Entities in Early Oncology Drug Development?" The Scientific World Journal, Aug. 18, 2014, (9 pages); https://doi.org/10.1155/2014/269605.

Mazar, A.P et al, "The Urokinase Plasminogen Activator System in Cancer: Implications for Tumor Angiogenesis and Metastasis," Angiogenesis 3, 15-32 (1999); https://doi.org/10.1023/A:1009095825561.

Mazar, A.P, "The Urokinase Plasminogen Activator Receptor (uPAR) as a Target for the Diagnosis and Therapy of Cancer," Anticancer Drugs, Jun. 2001;12(5):387-400; doi: 10.1097/00001813-200106000-00001 (Abstract only).

(56) References Cited

OTHER PUBLICATIONS

Wei, c. et al, "suPAR, a Circulating Kidney Disease Factor," Frontiers in Medicine, vol. 8, Oct. 6, 2021; doi: 10.3389/fmed.2021.745838.
Resnati, M. et al, "Proteolytic Cleavage of the Urokinase Receptor Substitutes for the Agonist-Induced Chemotactic Effect," EMBO J. Apr. 1, 1996;15(7):1572-82. PMID: 8612581; PMCID: PMC450067.
Resnati, M. et al, "The Fibrinolytic Receptor for Urokinase Activates the G Protein-Coupled Chemotactic Receptor FPRL1/LXA4R," Proc Natl Acad Sci U S A. Feb. 5, 2002;99(3):1359-64. doi: 10.1073/pnas.022652999.
Huang, C-Y et al, "Microdosimetry for Targeted Alpha Therapy of Cancer," Computational and Mathematical Methods in Medicine, vol. 2012 (2012), Article ID 153212, (6 pages); http://dx.doi.org/10.1155/2012/153212.
Leygue, N. et al, "Efficient Synthesis of a Family of Bifunctional Chelators Based on the PCTA[12] Macrocycle Suitable for Bioconjugation," European Journal of Organic Chemistry, vol. 2019, issue 18, May 15, 2019, pp. 2899-2913; https://doi.org/10.1002/ejoc.201900280 (Abstract only).
Wu, T.T. et al, "Possible Use of Similar Framework Region Amino Acid Sequences Between Human and Mouse Immunoglobulins for Humanizing Mouse Antibodies," Molecular Immunology, vol. 29, issue 9, Sep. 1992, pp. 1141-1146; https://doi.org/10.1016/0161-5890(92)90047-2 (Abstract only).
Studnicka, G.M. et al, "Human-Engineered Monoclonal Antibodies Retain Full Specific Binding Activity by Preserving non-CDR Complementarity-Modulating Residues," Protein Engineering, Design and Selection, vol. 7, Issue 6, Jun. 1994, pp. 805-814; https://doi.org/10.1093/protein/7.6.805 (Abstract only).
Kratochwil, C. et al, "225Ac-PSMA-617 for PSMA-Targeted $\alpha$-Radiation Therapy of Metastatic Castration-Resistant Prostate Cancer," Journal of Nuclear Medicine Dec. 2016, 57 (12) 1941-1944; doi: https://doi.org/10.2967/jnumed.116.178673.
Langbein, T. et al, "Future of Theranostics: An Outlook on Precision Oncology in Nuclear Medicine," Journal of Nuclear Medicine Sep. 2019, 60 (Supplement 2) 13S-19S; doi: https://doi.org/10.2967/jnumed.118.220566.
Eder, A,C. et al, "A New Class of PSMA-617-Based Hybrid Molecules for Preoperative Imaging and Intraoperative Fluorescence Navigation of Prostate Cancer," Pharmaceuticals 2022, 15, 267; https://doi.org/10.3390/ph15030267.

* cited by examiner

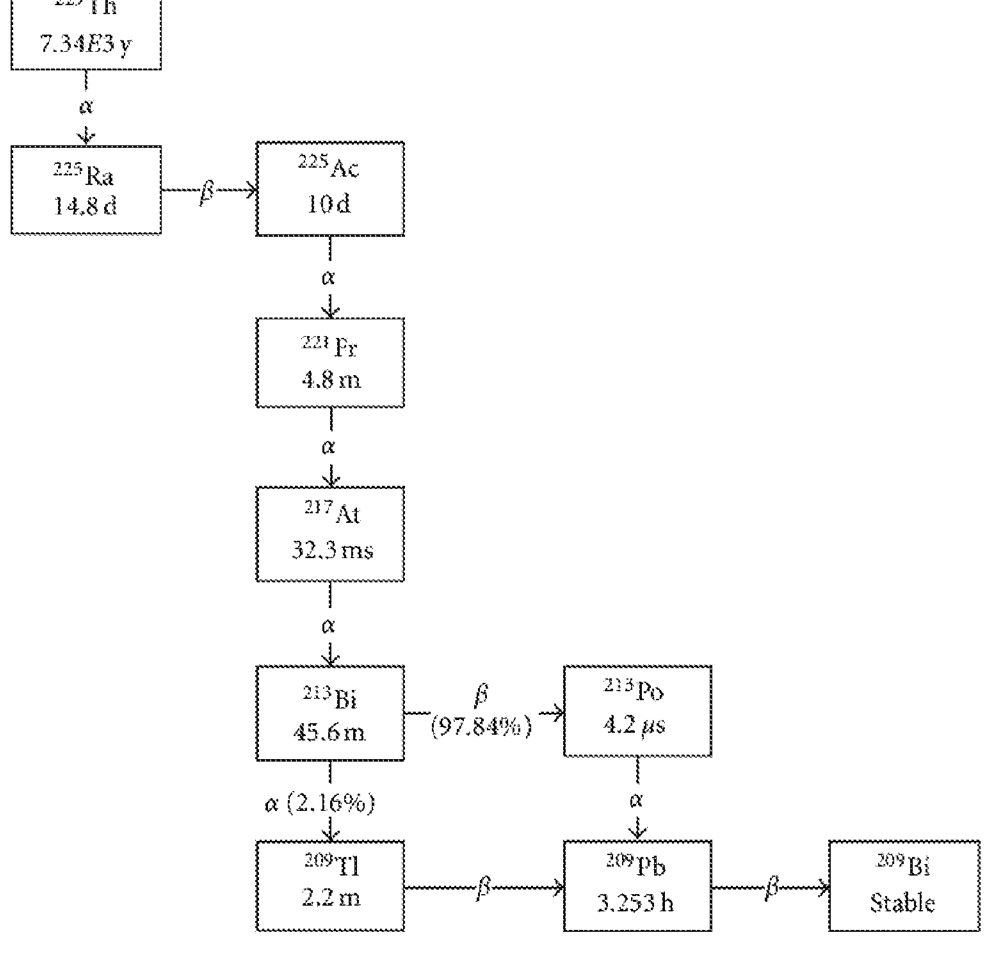
229Th
7.34E3 y
α
225Ra
14.8 d
β
225Ac
10 d
α
221Fr
4.8 m
α
217At
32.3 ms
α
213Bi
45.6 m
β
(97.84%)
213Po
4.2 μs
α (2.16%)
α
209Tl
2.2 m
β
209Pb
3.253 h
β
209Bi
Stable

UROKINASE PLASMINOGEN ACTIVATOR RECEPTOR-TARGETED RADIOPHARMACEUTICAL

CROSS-REFERENCE TO RELATED APPLICATIONS

This application claims priority to U.S. application Ser. No. 63/191,499 and Ser. No. 63/191,506, both filed on May 21, 2021, whose disclosures are incorporated herein by reference.

SEQUENCE LISTING

The sequence listing associated with this application is provided in text format in lieu of a paper copy and is hereby incorporated by reference into the specification. The name of the text file containing the sequence listing is 9975-130 ST25.txt the text file is 11 KB, was created on Jul. 5, 2022; and is being submitted via EFS-Web with the filing of the specification.

BACKGROUND OF THE INVENTION

Radiopharmaceuticals typically contain a radioisotope attached to a targeting moiety or carrier. The radioisotope is carried to the target by the carrier where it decays. The mode of isotope decay determines the type of radiopharmaceutical.

Typically, gamma emitting isotopes are used to detect the fate of the construct and are used for diagnostic purposes. Constructs with particle emitters are preferred for therapy. Although beta-emitting radionuclides were used previously, alpha-emitting radionuclides have shown excellent efficacy in recent years.

Alpha-emitting radionuclides are effective at killing cells in part due to the short particle range and high linear energy transfer (LET). Poty et al. [*J Nucl Med.* 2018 June: 59(60): 878-884] describe the use of alpha emitters for therapeutic radiopharmaceuticals.

The relatively long half-life of the alpha-emitting radionuclide actinium-225 (Ac-225) compared to other alpha emitters is one of the reasons that it has become popular as a therapeutic radioisotope for the treatment of cancer. Clinical trials with constructs using the isotope have shown excellent results. The about 10-day half-life is a good match for the in vivo biological half-life of monoclonal antibodies and the multiple alpha emissions produced by Ac-225 and its daughters were responsible for a high rate of tumor cell kill. However, the chemistry necessary to attach Ac-225 to a targeting moiety was lacking.

Ac-225 ions exhibit a valence of +3, with a documented ionic radius of 112 pm. Due to its lack of polarizability, $Ac^{+3}$ is classified as a "hard" Lewis acid according to the Hard and Soft Acids and Bases (HSAB) [Pearson, J Am Chem Soc 1963, 85:3533-3539] theory and is therefore likewise predicted to prefer "hard," nonpolarizable, electronegative Lewis bases such as anionic oxygen donors. The hard/soft acid-base properties of a specific ion can be quantified using the concept of absolute ($\eta$) chemical hardness. The absolute chemical hardness ($\eta$) of an ion is given by the equation $(\eta)=(I-A)/2$, where I is the ionization energy and A is the electron affinity of the species of interest. [Parr and Pearson, *J Am Chem Soc,* 1983; 105:7512-7516; and Pearson, *Inorg Chem* 1988; 27:734-740.]

Absolute chemical hardness of $Ac^{+3}$ and $La^{+3}$ so calculated are 14.4 eV and 15.4 eV, respectively. Soft ions such as $Au^{+}$, $Ag^{+}$ and $Cu^{+}$ exhibit absolute chemical hardness values that's range from 5.7 to 6.3 eV, whereas conventional hard ions, like $Sc^{+3}$ and $Al^{+3}$ are characterized by absolute chemical hardness values of greater than 24 eV. Thiele et al., *Cancer Biother Radio,* 2018 33(8):336-348.

The large ionic size of $Ac^{+3}$ is suited to large polydentate chelators of high denticities, because most commonly used chelates for Ac(III) range between 8-12 coordinate. Actinium is similar to other actinides and rare earth elements, and can undergo hydrolysis in solution in the absence of a chelating agent to form $[Ac(OH)_{3-x}]^{x-}$; the sub-picomolar concentrations of Ac-225 cause the hydroxide species in turn to form radiocolloids that bind to surfaces such as reaction vessels.

Emission of multiple alpha-particles in the Ac-225 decay chain makes Ac-225 a particularly effective isotope to kill cancer cells, yet also makes the directed delivery of the nuclide and its decay daughters a challenge. Due to the conservation of momentum, the emission of an energetic alpha particle imparts a recoil energy to the daughter nucleus often >100 keV, 1000 times larger than the binding energy for any chemical bond. This results in release of the daughter nuclide from the chelator of the original delivery vector. The subsequent redistribution of the alpha-emitting daughter nuclides in vivo can cause substantial harm to untargeted healthy tissues and reduce the therapeutic effect.

Davis et al., *Nuc Med Biol* 1999, 26(5):581-589 reported that limited information exists regarding the behavior of Ac-225 in vivo. Preliminary studies have evaluated Ac-225 complexed to citrate with respect to tissue uptake, biodistribution, and tumor tropism in animal models. Previous studies using Ac-225 complexed to either of the polyaminocarboxylate chelators, ethylenediamine tetraacetic acid (EDTA), or cyclohexyl diethylenetriaminepentaacetic acid (CHX-DTPA) showed varied tissue tropism and elevated blood clearance compared with uncomplexed Ac-225.

Ac-225-CHX-DTPA-monoclonal antibody (Mab) complexes used to determine biokinetic behavior on tumor-bearing nude mice showed successful in vitro complexing but poor stability in vivo. Thus, whereas Ac-225 can prove useful in radiotherapeutic models, information regarding potentially effective chelators and the relative stability of such Ac-225 complexes in vivo is lacking.

A recent review article on Ac-225 radio-pharmaceuticals, Robertson et al., *Curr Radiopharm,* 2018, 11(3):156-172, noted that the discovery of a chelating agent that binds Ac(III) with sufficient stability and that also controls the release of its daughter nuclides remains a challenge. Moreover, limited Ac-225 global availability of and the absence of a stable surrogate nuclide has limited the study of this isotope to a handful of institutions around the world that have secured a reliable Ac-225 supply.

The above review authors included the Davis et al. article, above, and noted that biodistribution profiles over the course of 8 days for each of the purified Ac-225-complexes were assessed by injecting 92 kBq (2.5 mCi) of each complex, and compared to the Ac-225-acetate biodistribution as a control.

Because uncomplexed Ac-225 accumulates predominantly in the liver with small amounts in the bone, kidney, and heart, high Ac-225 liver uptake of a chelate indicates an unstable complex in vivo. Cyclohexyldiethylenetriaminepentaacetic acid "a" isomer (CHX-A"-DTPA), and 1,4,7,10,13-pentaazacyclo-pentadecane-N,N',N",N'",N""-pentaacetic acid (PEPA) reduced liver uptake Ac-225 of the complex by more than 5.5 times compared to Ac-225 acetate, and although the Davis et al. data suggested-CHX-A"-DTPA to be the most effective tested chelator complex with regard to its in vivo stability, the Robertson et al., review authors wrote that "improvements can still be made to further reduce non-target tissue accumulation." [Robertson et al., at page 164.]

As such, CHX-A"-DTPA provides inadequate chelation of Ac(III). Another important finding of the initial in vivo study on which Robertson et al. commented was that the maximum tolerated dose of Ac-225-CHX-A"-DTPA was less than 185 kBq (5 mCi), because at doses of 185 kBq (5 mCi) or higher, severe tissue damage was observed as early as 1 hour post-injection (p.i.), which ultimately led to study animal death, causing 100% mortality by day 8 p.i.

Attachment of actinium to a targeting molecule was accomplished by Sheinberg's research group (Sheinberg, *Science* 2001 Nov. 16; 294(5546):1537-1540. doi: 10.1126/science.1064126). The chelator of choice was a bifunctional molecule based on DOTA. However, in the Sheinberg group's report, a two-step method was used to obtain enough Ac-225 on the targeting moiety. In addition, yields based on Ac-225 starting material were very low, less than 10% of the isotope was incorporated into the targeting moiety. More than 90% of the isotope was wasted. Specific activities with this process ranged from about 50 to 70 μCi per mg of antibody. Clearly, a one-step process with higher yields would be preferred.

Further studies of possible chelators by the Scheinberg research group [McDevitt et al., *App. Radiat. Isot.,* 2002, 57(6):841-847] found that of six possible chelators studied, showed that only DOTA and 1,4,7,10-tetraazacyclododecane-1,4,7,10-tetra-propionic acid (DOTMP) showed any complexation of Ac-225 after 2 hours at 37° C. with radiochemical yields (RCYs) of >99 and 78%, respectively. However, subsequent in vitro stability assays in serum suggested that the Ac-225 DOTA complex was robust, remaining >90% intact after 10 days, whereas the Ac-225-DOMTMP complex rapidly dissociated.

A two-step labeling process was again employed that required radiolabeling of the bifunctional DOTA-NCS ligand first, followed by mAb conjugation (pH 8.7, 37° C. for 52 minutes). Despite low overall radiochemical yields of only 9.8±4.5%, reasonable specific activity (4.1±2.6 GBq/g, or 0.11±0.07 Ci/g) was achieved that permitted preclinical therapeutic studies. Low yields were attributed to the first Ac-225 labeling step of DOTA-NCS that required heating and, consequently, degradation of the isothiocyanate linker resulting in poor mAb conjugation in the following step.

The Scheinberg group and co-workers [McGuire et al., *J. Nucl. Med.,* 2014, 55(9):1492-1498] later reported a one-step process for preparation of Ac-225-DOTA-antibody constructs. That process proceeded in 2 M tetramethyl ammonium acetate buffer (pH 7.5) with the addition of L-ascorbic acid as radioprotectant to the addition of DOTA-antibody construct and Ac-$225^{+3}$ with a typical final reaction pH value of 5.8. Heating to 37° C. for 2 hours allowed a 10-fold increase in radiochemical yield (80%) compared to previous 2-step methods (6-12%), and resulted in the preparation of bioconjugates with up to 30-fold higher specific activities (120 GBq/g compared to 3.7-14.8 GBq/g). The highest specific activity achieved was equivalent to 1 actinium for every 25 antibodies.

US 2004/0067924 A1 (Frank) teaches the use of 12-membered macrocyclic amine-based polyacetate and polyphosphonate chelating agents for complexing Ac-225. DOTA-based chelating agents were found useful for chelating Ac-225.

Paragraph [0082] of that patent publication noted that the nitrobenzyl group of one depicted DOTA chelant can be reduced to an aniline, whose amine can be subsequently converted to an isothiocyanate to form a bifunctional compound for linking to a targeting peptide antibody or other entity. A bifunctional analog of PCTA (below) was said could be prepared by attaching a linking group to one of the acetate carbons.

Chelating agents based 3,6,9,15-tetra-azabicyclo-[9.3.1]pentadeca-1(15),11,13-triene-3,6,9-acetic acid (PCTA) were mentioned in the text of the Frank application and binding data with actinium were shown. The PCTA compound shown and utilized was not adapted for linkage to a targeting molecule such as a peptide or antibody other than by the possible use of one of the chelating carboxyl groups. No disclosure of a targeted construct using PCTA was disclosed.

Yapp et al., *Mol Imaging June* 2013 12(4):263-272 reported on the use of PCTA, DPTA and 1-oxa-4,7,10-triazacyclododecane-4,7,10-triacetic acid (Oxo-DO3A) for the chelation of Cu-64 [Cu (II)-64] for use in PET scan studies of tumor vasculature. The chelates were bonded to the cyclic tetrapeptide cyclic-(RGDyK) via benzylisothiocyanate linkages to the added lysine of the cyclic peptide.

An earlier one-step process was disclosed in Simón, WO 2011/011592 A1. This patent application teaches the preparation of a protein conjugated with chelators as a first step. After removal of excess chelating agent, the protein-chelated conjugate was reacted with the isotope. Again, a DOTA-based chelator was used for the work showing that the still current thinking in the art was that DOTA-based chelators would be the best for Ac-225.

The method in the Simón disclosure required the use of high concentrations of acetate ion and a high chelator to antibody ratio (CAR). Starting reactions were conducted using a molar reactant ratio of 100 chelators per antibody to yield a CAR number of 10-12.

It is desirable to produce high specific activity Ac-225 constructs with conjugates that have a lower CAR number. This is because as the CAR number increases, the biological targeting of the antibody decreases. Thus, even though the one-step process is taught with Ac-225 and DOTA type chelators, the CAR numbers required were high using DOTA-type chelating agents. Clearly there is a need for better chelating agents for preparing Ac-225 constructs.

The difficulties in using DOTA as a chelating agent for Ac-225 as discussed above notwithstanding, Thiele et al., *Cancer Biother Radio,* 2018 33(8):336-348, as recently as 2018 used the phrase "DOTA: the current gold standard" (at 340) for a section of their review. The last sentence of those authors' DOTA section reads: "Collectively, these shortcomings indicate that DOTA is not ideal for use in $^{225}$Ac-TAT [$^{225}$Ac targeted alpha therapy] applications, highlighting the need for more suitable chelating scaffolds for $^{225}$Ac."

The chemistry associated with attaching Ac-225 to targeting moieties has been challenging for the users and writers. It is apparent that better methods of attaching Ac-225 to molecules are needed. The present invention helps address that need. Surprisingly, we have found that PCTA-based chelating agents form stable chelates with Ac-225 under mild conditions and at lower CAR numbers than were previously reported when using DOTA, the prior "GOLD standard". In addition, our data show that daughter Bi-213 ions are also retained by the PCTA-based chelating agents so that little if any of the radioactivity travels to other than the locus of the selected target.

Bi-213 is a radioactive decay product of Ac-225, whereas Bi-212 produced by the radioactive decay of lead-212 (Pb-212) after step-wise decay of uranium-234 (U-234). The short half-life of Bi-212 and Bi-213 can limit the application of these radionuclides in radionuclide therapy.

Bismuth isotopes, Bi-212 and Bi-213, are also candidates for use in radioimmunotherapy. Several preclinical studies have been published utilizing one, the other or both isotopes.

Illustratively, Park et al., *Blood,* 2020 116(20):4231-4239, reported a preclinical study in mice having xenografts of Ramos lymphoma that were treated with anti-CD20 antibody fused to streptavidin followed by [213Bi]DOTA-biotin. The treated mice with tumors exhibited marked growth delays and mean survival times about four-times longer than untreated controls. A review by Yong et al., *AIMS Med Sci,* 2021, 2(3):228-245, discussed recent work using Pb-212/Bi-212 in targeted a-particle therapy (TAT), such as work that utilized the chelator 2-(4-isothio-cyanatobenzyl-1,4,7,10-tetraaza-1,4,7,10-tetra-(2-carbamonylmetyl)cyclododecane (TCMC) linked to a mAb, trastuzumab, that binds to HER2. A review by Mulford et al., *J Nucl Med* 2005, 46(1 Suppl):199S-204S discusses several TAT therapies that utilize one or the other of the above bismuth isotopes.

The labeling of biomolecules with precursor Pb-212 instead of Bi-212 or Bi-213, as discussed in Yong et al., above, has the advantage of obtaining a conjugate with a half-life of 10.6 hours, compared with of 60 minutes for Bi-212 or 46 minutes for Bi-213. Previous attempts to prepare a potential in vivo generator with Pb-212 complexed by the DOTA chelator failed, because about 36% of Bi was reported to escape as a result of the Pb-212 decaying via a beta particles to form Bi-212, which were not held by DOTA. It can be important that Bi-212 formed in the decay of Pb-212 remain bound to the carrier because free bismuth ions localize in the kidneys. Bartos et al., *J Radioanal Nucl Chem,* 2013 295:205-209.

Zirconium-89 is another useful radioisotope in that zirconium has a valence and the Zr-89 emits a gamma ray (909 keV) and also a positron at about 397 keV, both emissions being useful in diagnostics. The half-life of Zr-89 is 3.3 days, which is similar to the circulation half-lives of many monoclonal antibodies used in medicine. Those isotopes have been used in radiolabeling and evaluation of mAbs in positron emission tomography (Immuno-PET). [Saleem et al., *Sci World J* 2014, Article ID 269605, 9 pages.] The final decay product of Zr-89 is yttrium-89, a stable non-radioactive isotope.

A further useful isotope in the present invention is indium-111. Indium also has a valence of +3, and In-111 has a half-life of about 2.8 days. Indium-111 decay provides gamma rays of 0.171 MeV and 0.245 MeV, that can be used in diagnostic scans such as single photon emission computed tomography (SPECT) imaging. In-111 decays to cadmium-111, which is non-radioactive and stable.

A significant body of evidence from studies in vitro and in vivo has established that the urokinase plasminogen activator (uPA) system is central to the process of metastasis, making it a promising target for cancer drug development (Mazar, et al., 1999 *Angiogenesis* 3:15-32). In addition to uPA, its cell surface receptor (uPAR) is a suitable target for the design and development of cancer therapeutic and diagnostic agents (Mazar, 2001 *Anti-Cancer Drugs* 12:397-400) because:

(a) uPAR is selectively expressed on metastatic tumor cells and angiogenic endothelial cells ("ECs"), but not on other cells;

(b) uPAR is an important participant in several extracellular and intracellular pathways required for metastasis that are currently the object of intense drug development efforts; and (c) it is possible to interfere at several different points along the uPA pathway. Thus, uPA and uPAR are promising targets for the development of diagnostics and therapeutics useful against many different types of tumors/cancers.

A soluble form of uPAR referred to in the art as "suPAR" is also a useful target. suPAR was detected in many body fluids, such as plasma, serum, urine, saliva, and cerebrospinal fluids. Since then, the elevation of circulating suPAR has been documented in many disease states, reflecting the activation state of the immune system Wei et al., (October 2021) *Front Med.* 8:745838).

uPAR has three extracellular domains that are designated D1, D2 and D3 from the amino-terminal end of the protein toward the carboxy-terminus. Several enzymes have been reported to cleave those domains between D1 and D2 to provide domains D2 and D3 as suPAR. Activation of soluble recombinant uPAR can be achieved in vitro by cleavage with chymotrypsin between domains D1 and D2, generating a carboxyl-terminal fragment starting at residue 88 ($D2D3_{88-274}$) as discussed by Resnati et al. [1996 *EMBO J* 15(7):1572-1682 and 2002 *Proc Natl Acad Sci, USA* 99(3): 1359-1364]. The present anti-suPAR mAbs were induced by a soluble form of suPAR expressed in *Drosophila* S2 cells that express a minimally glycosylated isotype of suPAR.

An antibody (Ab) also known as an Immunoglobulin (Ig) is the large Y shaped protein produced by the body's immune system when it detects harmful substances, called immunogens like bacteria and viruses. The production of antibodies is a major function of the immune system and is carried out by a type of white blood cell called a B cell (B lymphocyte), differentiated B cells called plasma cells. The produced antibodies bind to specific portions of the immunogen called antigens that are expressed in external factors and cell surface structure such as those on cancer cells like uPAR.

Antibodies are heavy (about 150 kDa) globular plasma proteins. The basic structures of all antibodies are same.

A typical mammalian antibody, except for those of camelids as discussed hereinafter, contain four polypeptide chains: two identical heavy chains and two identical light chains connected to each other and themselves by disulfide bonds. A light chain (L) is a polypeptide of about 22,000 Da and heavy chain (H) is a larger polypeptide having a mass of about 50,000 Da or more. There are five types of Ig heavy chain denoted by the Greek letters: $\alpha$, $\delta$, $\varepsilon$, $\gamma$, and $\mu$. There are two types of Ig light chain, which are called lambda ($\lambda$) and kappa ($\kappa$).

Each antibody heavy and light chain contains a N-terminal variable region followed by a constant region. The variable (V) region consists of about 100 to 110 amino acids and differ from one antibody to another. Each variable region contains three complementarity determining regions (CDRs) separated by four framework regions. The CDRs are primarily sequences that bind to the antigenic region of the immunogen.

The remainder of each heavy and light chain in the molecule is a constant (C) region that exhibits limited variation that defines the two light chain subtypes and the five heavy chains subclasses. The heavy chains contain three constant regions (CH1, CH2 and CH3), whereas the light chain contains only one constant region (CL).

Some heavy chains (α, δ, γ) also contain a proline-rich hinge region. Effector functions are mediated by the carboxy-terminal domains. The ε and μ heavy chains, which lack a hinge region, contain an additional domain in the middle of the molecule.

The 5 antibody types—IgG, IgM, IgA, IgD, IgE—(isotypes) are classified according to the type of heavy chain constant region, and are distributed and function differently in the body. The IgG isotype, of particular interest here, has four human subclasses ($IgG_1$, $IgG_2$, $IgG_3$ and $IgG_4$), each containing a different heavy chain. They are highly homologous and differ mainly in the hinge region and the extent to which they activate the host immune system. $IgG_1$ and $IgG_4$ contain two inter-chain disulphide bonds in the hinge region, whereas $IgG_2$ has 4 and $IgG_3$ has 11. Those isotypes are themselves further divided that are not discussed herein.

The invention disclosed below teaches the using a particular targeting species molecule and a single chelating agent for both therapeutic and diagnostic (theranostic) uses, providing a single chelator-linked targeting system for both uses. Such a theranostic has significant benefits in development and manufacturing as the targeting species and chelation manufacturing steps can be common with the labeling of the radioisotope being distinct. This provides some time and cost advantages in development, toxicity studies with the unlabeled targeted-chelator, common stability and bulk drug substance.

SUMMARY OF THE INVENTION

This invention relates to the use of a chelating agent containing a 12-membered macrocyclic amine with a pyridine ring imbedded in the structure that surprisingly easily makes stable metal ligand complexes with trivalent radioactive isotope ions such as Ac-225, Bi-212, Bi-213, Zr-89 and In-111, and also with a particular targeting species molecule to form a radiotherapeutic agent or a radiodiagnostic agent (or generically, a radiopharmaceutical agent). These radiopharmaceuticals can also be referred to as radiotheranostic agents.

The chelating agent is bonded to the particular targeting species molecule while permitting the chelation of the $Q^{+3}$ ion to that part of the molecule. Thus, the chelating agent is bonded to a part of the targeting molecule that does not interfere with the ability of the targeting molecule to reach its target. The targeting species binds the radiopharmaceutical agent to cells that are to be killed or one or more of whose presence, location, size and shape are to be determined.

More specifically, a targeting species is chemically-bonded to a PCTA chelator with its chelated trivalent radioactive isotope ion, $Q^{+3}$, to form the theranostic radiopharmaceutical that has the general structural formula shown below in Formula I and which, depending on the radioactive isotope that is chelated, can be used therapeutically to kill targeted cells or to bind to targeted cells to signal the one or more of the presence, location, size or shape of the bound cells

I

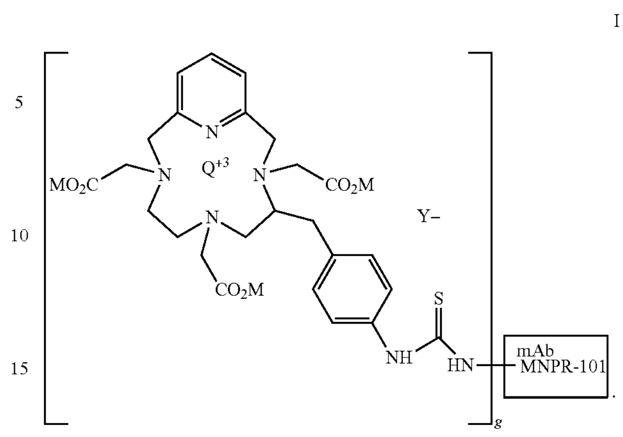

In the above Formula, M is a proton (H+), an ammonium ion or an alkali metal ion. The boxed mAb MNPR-101 represents the chemically-bonded humanized mAb MNPR-101 or a paratope-containing portion thereof prepared from the humanized mouse monoclonal antibody ATN-658 having ATCC Accession Number PTA-8191. "g" is a number whose average value is about 1 to about 12 that indicates the average number of chelated PCTA-chelated trivalent radioactive ions per each molecule of mAb MNPR-101 or a paratope-containing portion thereof. Illustrative chelated Q+3 ions include trivalent Ac-225, Bi-213, Bi-212, Zr-89 or In-111. An optional anion, Y−, can be present in an amount needed to balance the ionic charge.

The chelation reaction with the $Q^{+3}$ ion can be performed first followed by attachment to the targeting species molecule, T. This is referred to as a two-step process because the isotope is handled twice. Alternatively, the conjugation reaction (attaching the chelating agent to the targeting species) can be accomplished first followed by insertion of $Q^{+3}$ ion. This is called a one-step process as the isotope is only handled once, and is preferred. Actinium-225 is a preferred $Q^{+3}$ ion.

In accordance with the invention, the radiopharmaceutical uses a particular monoclonal antibody (mAb) or paratope-containing portion thereof as the targeting species molecule that is chemically-bonded the chelating agent that chelates a trivalent radioactive isotope, $Q^{+3}$ ion. More specifically, that mAb is a humanized antibody or an antigen-binding fragment thereof that binds to urokinase plasminogen activator cell surface receptor (uPAR) itself and to the binary uPA-uPAR complex; i.e., uPAR, and to a complex formed from uPAR and urokinase plasminogen activator (uPA).

The humanized antibody or paratope-containing portion (or antigen-binding fragment) thereof comprises the structural elements below. The humanized antibody is an IgG1 kappa light chain subgroup 2 (VK2) type. A preferred mAb is designated MNPR-101 and is a humanized version of mouse monoclonal ATN-658. mAb ATN-658 is produced by a hybridoma having ATCC Accession #PTA-8191. Monoclonal antibody (mAb) MNPR-101 is discussed in detail hereinafter.

The antibody or antigen-binding fragment comprises:

(A) a $V_L$ kappa chain comprising three CDRs, CDR L1, CDR L2 and CDR L3, that have the respective sequential combination of amino acid residue sequences, respectively, SEQ ID NO:3, SEQ ID NO:4 and SEQ ID NO:5; and (B) a $V_H$ chain comprising three CDRs, CDR H1, CDR H2 and CDR H3, that have the respective sequential type 1 combination of amino acid residue sequences SEQ ID NO:10, SEQ ID NO:11 and SEQ ID NO:12.

In one embodiment, the kappa chain variable region has the amino acid residue sequence of SEQ ID NO: 1. In another embodiment, the kappa chain variable region has the amino acid residue sequence of SEQ ID NO: 2. The kappa chain constant region has the amino acid residue sequence of SEQ ID NO: 7.

In one embodiment, the heavy chain variable (VH) region has the amino acid residue sequence of SEQ ID NO: 8. In another embodiment, the heavy chain variable region has the amino acid residue sequence of SEQ ID NO: 9. The heavy chain type 1 constant region (CH1, CH2 and CH3 domains together) has the amino acid residue sequence of SEQ ID NO: 14.

A pharmaceutical composition is contemplated that comprises a theranostic effective amount of a targeted radiopharmaceutical of Formula I dissolved or dispersed in a pharmaceutically acceptable diluent. Preferably, the pharmaceutically acceptable diluent is an aqueous liquid at ambient temperature and is adapted for parenteral administration.

In one embodiment, that pharmaceutical composition is used in a method for treating a mammalian host having a disease, disorder or condition characterized by undesired angiogenesis, tumor growth and/or tumor metastasis comprising administering to the host a targeted cell-killing (therapeutic) effective amount of the targeted radiopharmaceutical.

In further embodiments, a contemplated targeted radiopharmaceutical is used as a diagnostic agent. As such, the invention contemplates a method for assaying a mammalian host thought or known to have a disease, disorder or condition characterized by undesired angiogenesis, tumor growth and/or tumor metastasis by administering to the host a target cell-binding effective amount of the targeted radiopharmaceutical followed by scanning the host to detect and locate the radiation emitted by the bound targeted radiopharmaceutical.

BRIEF DESCRIPTION OF THE DRAWING

In the drawing forming a portion of this disclosure,

FIG. 1 shows the radioactive decay scheme from $^{229}$Th to stable $^{209}$Bi via $^{225}$Ac in the development of the preparation of $^{213}$Bi, showing the emission of four alpha particles (α) and four beta rays (β) as well as the half-life of each radionuclide in the decay scheme as shown in Huang et al., *Comput Math Method M, Vol.* 2012, Article ID 153212, 6 pages;

DETAILED DESCRIPTION OF THE INVENTION

This invention relates to a targeted radiopharmaceutical that comprises a monoclonal antibody (mAb) or paratope-containing portion thereof targeting species that is chemically-bonded a chelating agent, PCTA (discussed hereinafter), that chelates a trivalent radioactive isotope, $Q^{+3}$ ion.

The trivalent radioactive ion, $Q^{+3}$, is chelated by PCTA that is chemically-bonded (linked) to a humanized monoclonal antibody that targets and binds to (immunoreacts with) the binary urokinase plasminogen activator (uPA)-urokinase plasminogen activator receptor (uPAR) complex (uPA-uPAR) and also specifically binds to uPAR at a location that does not interfere with uPA-uPAR binary complex formation. A contemplated targeted radiopharmaceutical of this invention has the general structural formula shown below in the Formula I

I

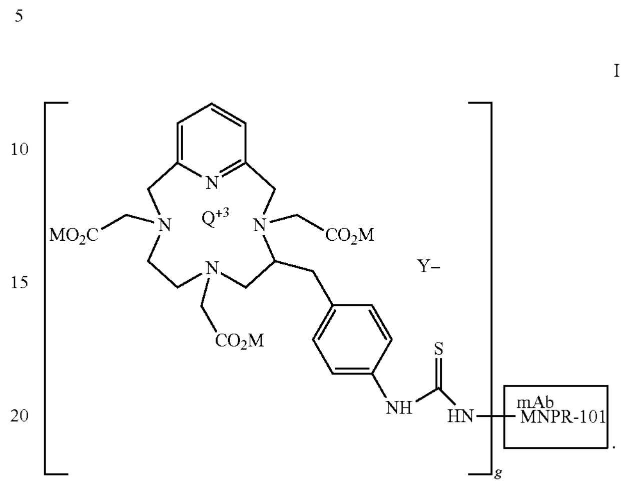

In the above Formula, M is a proton (H+), an ammonium ion or an alkali metal cation. The boxed mAb MNPR-101 represents the chemically-bonded humanized mAb MNPR-101 or a paratope-containing portion thereof prepared from the humanized mouse monoclonal antibody ATN-658 having ATCC Accession Number PTA-8191. "g" is a number whose average value is 1 to about 12, indicating the average number of chelated PCTA-chelated trivalent radioactive ions per each molecule of mAb MNPR-101 or a paratope-containing portion thereof. An optional anion, $Y^-$, can be present in an amount needed to balance the ionic charge.

The humanized antibody or paratope-containing portion (or antigen-binding fragment) thereof comprises the structural elements below. The humanized antibody is an IgG1 kappa light chain subgroup 2 (VK2) type monoclonal antibody. The mAb is designated MNPR-101 and is a humanized version of mouse monoclonal ATN-658 that is produced by a hybridoma having ATCC Accession #PTA-8191.

Some versions of the chelating agent are referred to as pyridine-based 12-membered tetraaza-macrocyclic ligands or PCTA (First published: 2 Apr. 2019 chemistry-europe-.onlinelibrary.wiley.com/-doi/abs/10.1002/ejoc.201900280.

The number of chelators bonded per antibody molecule, g, is an average number because some antibodies of an otherwise homogeneous monoclonal antibody preparation may not react whereas others react well. Average numbers of chelators bonded per antibody molecule are 1 to about 12, preferably about 3 to about 12, and more preferably about 8 to about 10 when an isothiocyanate group from the chelator is being bonded to an intact antibody. Where a paratope-containing portion (or antigen-binding fragment) thereof is the targeting species, the number of PCTA chelators per targeting species molecule tend to be fewer such as about 1 to about 5 as there are fewer reactable groups such as lysine amino groups with which the isothiocyanate group can react when the two pairs of CH2 and CH3 portions of the heavy chain are absent.

The preferred chelator is referred to in the art as PCTA. The chemical formula for a particularly preferred form of PCTA is the unreacted isothiocyanate linking group that enables the chelator to be bifunctional, and is shown in Formula II, below, where M is as before described.

II

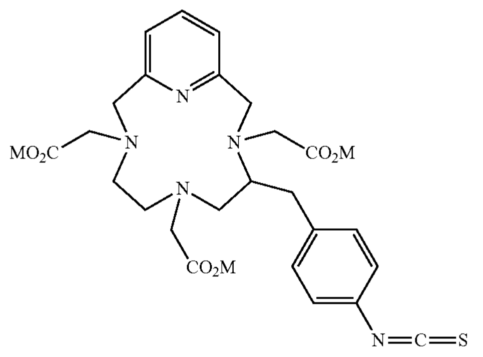

The chelator of Formula II is commercially available from Macrocyclics Inc. (Dallas, TX), under the designation p-SCN-Bn-PCTA.

A contemplated targeting species in this invention is the monoclonal antibody (mAb) MNPR-101, or a paratope-containing portion thereof. Once bound to a target cell, the antibody and its chemically-bonded PCTA that is chelated to a trivalent radioactive isotope, $Q^{+3}$ ion, such as the preferred Ac-225 ion can be taken into the unwanted cell at which time the Ac-225 or one of its daughter atoms can decay to release its cytotoxic alpha particle within the unwanted cell.

The term "antibody" is meant to include both intact mAb MNPR-101 molecules as well as antigen-binding fragments (paratope-containing portions) thereof, that can be produced by proteolytic cleavage of Ig molecules or engineered genetically or chemically. MNPR-101 is an IgG1 κ mAb that specifically binds to (immunoreacts with) an uPa-uPAR binary complex.

Paratope-containing portions or antigen-binding fragments include, for example, Fab, Fab', $F(ab')_2$ and Fv, each of which is capable of binding antigen. These fragments lack the Fc fragment of intact antibody (Ab) and have an additional advantage, if used therapeutically, of clearing more rapidly from the circulation and undergoing less non-specific tissue binding than intact antibodies.

Papain treatment of intact Ig's produces Fab fragments; pepsin treatment produces $F(ab')_2$ fragments. These fragments can also be produced by genetic or protein engineering using methods well known in the art.

A Fab fragment or portion is a dimeric protein consisting of the portion of an Ig molecule containing the immunologically active portions of an Ig heavy (H) chain and an Ig light (L) chain covalently coupled together and capable of specifically combining with antigen. Fab fragments are typically prepared by proteolytic digestion of substantially intact Ig molecules with papain using methods that are well known in the art. However, a Fab fragment can also be prepared by expressing in a suitable host cell the desired portions of Ig H chain and L chain using methods well known in the art.

A $F(ab')_2$ fragment is a tetramer that can be formed by pepsin cleavage of an intact antibody at a position carboxy-terminal to the intact antibody hinge position. Several smaller portions of the Fc fragment are also typically produced during pepsin cleavage, whereas papain cleavage typically produces a single Fc dimer.

The Fv fragment is a multimeric protein containing the immunologically active portions of an Ig H chain variable (V) region ($V_H$) and an Ig L chain V region ($V_L$) covalently coupled together and capable of specifically combining with antigen. Fv fragments are typically prepared by expression of the desired portions of Ig $V_H$ region and $V_L$ region in suitable host cells using methods well known in the art.

DNA sequences encoding the V regions of the H chain and the L chain are ligated to a linker that encodes a sequence of at least about 4 amino acid residues (typically small neutral amino acids). The protein encoded by this fusion permits assembly of a functional variable region that retains the specificity and affinity of the original Ab.

The mAbs contemplated herein were generated by immunization of Balb/c mice with the D2D3 domain of suPAR conjugated to KLH, followed by subsequent fusion studies that generated parental clones with specific cross-reactivity with the D2D3 domain of uPAR as determined by western blotting and ELISA assays using recombinant proteins. These parental clones were subjected to limiting dilution and a panel of mAbs specific for D2D3 was obtained. The properties of four of these Abs are summarized in the Table below. Isotyping identified all clones as IgG1, κ. Specificity for uPAR was confirmed by western blotting. The affinity of the mAbs was determined using direct binding assays. As is seen, three of the five mAbs exhibited affinities of about 1 to about 5 nM.

| Clone Name | Isotype | $K_D$ (nM) |
|---|---|---|
| ATN-615 | IgG1, κ | 2 |
| ATN-658 | IgG1, κ | 1 |
| ATN-616 | IgG1, κ | 5 |
| ATN-617 | IgG1, κ | 29 |

The mAb used herein designated mAb MNPR-101 is a humanized version of mouse mAb ATN-658, whose hybridoma has ATCC Accession Number PTA-8191, disclosed and claimed in U.S. Pat. No. 8,101,726. Mouse mAb ATN-615 that is also disclosed and claimed in U.S. Pat. No. 8,101,726, is secreted by a hybridoma that has ATCC Accession Number PTA-8192. The mAb MNPR-101 paratopic amino acid residue sequence (CDR; complementarity determining region; variable region) is almost identical (about 95.8%) to that of ATN-658, whereas the heavy chain constant regions (CH1, CH2 and CH3) are those of a human IgG1 antibody.

Humanization of ATN-658 to prepare MNPR-101 utilized the Xoma HE™ synthesis platform that utilizes the human antibody amino acid residue sequences reported in Wu and Kabat, 1992 *Mol. Immunol.,* 29(9):1141-1146 (hereinafter Kabat) combined with the sequences of the variable regions of the antibody to be humanized to form one or more consensus sequences. There are several steps in this process:

(1) Human Engineer™ (HE™) the ATN-658 Light and Heavy chains using the XOMA Corp. (Emeryville, CA) proprietary HE™ method to generate the low risk and low plus moderate risk HE™ variants;

(2) HE™ Variable (V) region sequences codon optimization, energy minimization and gene synthesis;

(3) Clone the 4 HE™ V regions into XOMA's proprietary transient expression vectors which contain human Gamma-1 and Kappa constant region modules;

(4) Transiently express the HE™ variants;

(5) Purify the humanized antibodies and characterize them for purity and endotoxin; and (6) Verify the affinity of the 4 HE™ variants.

The phrase "low risk" discussed above and hereinafter relates to whether a mouse-to-human amino acid residue change results in a major reduction in therapeutic immunogenicity with little chance of affecting binding affinity. The second phrase "high risk" relates to modifying positions at which a mouse-to-human amino acid residue change results in a degradation or abolition of binding activity with little or no actual reduction in therapeutic immunogenicity.

Humanization of ATN-658 to create mAb MNPR-101 using the Xoma HE™ platform was performed pursuant to the "low risk", "moderate risk" and "high risk" substitutions suggested in the following publications, patents and application: 1) WO 93/11794 "Methods and materials for preparation of modified antibody variable domains and therapeutic uses thereof"; 2) U.S. Pat. No. 5,766,886 "Modified antibody variable domains"; 3) U.S. Pat. No. 5,770,196 "Modified antibody variable domains and therapeutic uses thereof"; 4) U.S. Pat. No. 5,821,123 "Modified antibody variable domains"; 5) U.S. Pat. No. 5,869,619 Modified antibody variable domains, and 6) Studnicka et al. 1994 *Protein Eng* 7:805-814, all of whose disclosures are incorporated by reference.

Humanization of Variable (V) Region Amino Acid Residue Sequence of Mouse mAb ATN-658

The consensus amino acid sequence (single-letter code) of the light chain variable region ($V_L$) and heavy chain variable region ($V_H$) polypeptides of mAb ATN-658 are set out in U.S. Pat. No. 8,191,726 to Parry and Mazar, will not be repeated here and are incorporated by reference. cDNA was prepared from total RNA extracted from the hybridoma expressing ATN-658 and the variable regions were cloned, amplified and sequenced using standard techniques.

Following the course set out by Studnicka et al., above, human V kappa light chain subgroup 2 (VK2) and human heavy chain subgroup 1 (VH1) consensus sequences were utilized. The cognate mouse signal sequences were retained.

Two sequences for each of the light chain and the heavy chain variable regions were prepared. One sequence for each chain contained only low risk changes and the other sequence that contained both the low risk and the moderate risk changes were prepared for the VK2 and VH1 regions, providing a total of four sequences. Ten low risk and 1 moderate risk changes were introduced into the light chain framework sequences and 11 low risk and 5 moderate risk changes were introduced into the heavy chain framework sequences. Low risk residue position changes, those exposed to solvent but not contributing to antigen binding or antibody structure, are likely to decrease immunogenicity with little or no effect on binding affinity.

The amino acid residue sequences were sent to Blue Heron Biotech LLP, (Bothell, WA) for codon (Chinese Hamster Ovary cells) and expression optimization. The optimized DNA sequences were received and sent back to Blue Heron for gene synthesis.

Transient Expression Vector Construction

Codon- and expression-optimized low risk and low plus moderate risk Human Engineered™ light chains and heavy chains were cloned in-frame into XOMA's proprietary transient antibody expression vectors that contain human kappa and gamma-1 constant region modules. The DNA sequences were verified (at ELIM Biopharmaceuticals, Inc., Hayward, CA) prior to initiating expression.

Production of Human Engineered™ ATN-658 Antibodies

The four HE™ ATN-658 variants (referred to as HE™ ATN-1, HE™ ATN-2, HE™ ATN-3 and HE™ ATN-4) were produced by transient transfection in HEK293E cells. XOMA's transient transfection approach is described in detail in a poster presented at the 2005 ASCB Annual Meeting.

Briefly, the light and heavy chains were co-transfected into XOMA's suspension-adapted HEK293E cells grown in IS293 medium (Irvine Scientific, Irvine, CA) using 2 liter shake flasks. After 24 hours in shake flasks, 200 ml of transfected cells were centrifuged, resuspended in 40 ml of fresh medium and transferred to Integra flasks (Wilson Wolf Manufacturing, Inc., New Brighton, MN) for production. After incubation for seven days, the cell suspensions were removed from the Integra flasks, centrifuged and the culture supernatants retained. Antibodies in the culture supernatants were purified on protein A spin columns (Pro-Chem), dialysed against PBS, concentrated and sterile filtered.

The variable region constituent sequences of those four antibodies are illustrated in Table 1, below.

TABLE 1

| Antibody | Risk Level | | % Human |
|---|---|---|---|
| Variant | Heavy Chain | Light Chain | (as IgG1)* |
| HE ™ ATN-1 | Low | Low | 95.2 |
| HE ™ ATN-2 | Low | Low + Moderate | 95.2 |
| HE ™ ATN-3 | Low + Moderate | Low | 95.8 |
| HE ™ ATN-4 | Low + Moderate | Low + Moderate | 95.8 |

*Low or Low + Moderate Risk changes and conservation between mouse and human V regions wherein mouse amino acid residues are represented at any given position in at least two Kabat human V regions from matching subtype.

Concentration was determined by $A_{280}$ using an extinction coefficient of 1.52. The proteins were analyzed for purity by SDS-PAGE (4-20%) and for endotoxin using an LAL assay. Purification results demonstrate that all of the antibody preparations had concentrations≥1 mg/ml, were >90% pure and had low levels of endotoxin (<1 EU/mg).

Evaluation of Affinity of Human Engineered™ ATN-658 Antibodies by Biacore Assay Method Kinetics analysis of mouse monoclonal antibody ATN-658 and Human Engineered™ ATN-658 variant antibodies was conducted on a Biacore 2000® surface plasmon resonance instrument analyzer (Uppsala, Sweden) to produce sensograms based on the antibody-surface interactions. Kinetic determinations were performed using a capture method.

Mouse parental mAb ATN-658 was diluted in PBS to 2 μg/mL and injected over a rabbit anti-mouse capture surface. The HE™ variants were diluted to 1 μg/mL and injected over a protein A/G surface. Antibody injections were optimized to produce antibody densities of 100-200 RU.

Six serial 3-fold dilutions of soluble uPAR (suPAR) were prepared in running buffer (PBS), and each dilution was injected in triplicate in random order at 25° C. Buffer injections were evenly distributed throughout the run. The sample injections were double-referenced against the blank flow cells and buffer injections to correct for any bulk shift or non-specific binding. Data were analyzed with BiaEvaluation software from Biacore®. Sensorgrams were fit utilizing a 1:1 Langmuir model.

Humanized mAb MNPR-101

As compared to mAb ATN-658, one residue was changed in one CDR of each of the VK2 and VH1 regions in mAb MNPR-101 as compared to the CDR sequences of mAb ATN-658 (CDR L1 and CDR H2) in arriving at the six CDRs of mAb MNPR-101. The complementarity-determining regions (CDRs) for each variable region that are present in paratopic regions of mAb MNPR-101 and are set out in Table 2, below.

TABLE 2

Characteristics of CDRs of MNPR-101 L and H Chains

| CDR* | No. of Residues | Sequence1 | SEQ ID NO |
|---|---|---|---|
| CDR L1 | 16 | RSSQSLLDSDGKTYLN | 3 |
| CDR L2 | 7 | LVSKLDS | 4 |
| CDR L3 | 9 | WQGTHFPLT | 5 |
| CDR H1 | 10 | GYSFTSYYMH | 10 |
| CDR H2 | 17 | EINPYNGGASYNQKIQG | 11 |
| CDR H3 | 10 | SIYGHSVLDY | 12 |

*CDR L1: first CDR of L chain; CDR H2: $2^{nd}$ CDR of H chain, etc.

Sequences

Sequences for the VL and VH as well as the CL and CH regions of the Fab portion of mAb MNPR-101, and also the low risk sequences of the variable regions of both chains (HE ™ ATN-1) are shown below.

SEQ ID NO: 1-[mAb MNPR-101 VL]
Asp Val Val Met Thr Gln Ser Pro Leu Ser Leu Ser Val
Thr Ile Gly Glu Pro Ala Ser Ile Ser Cys Arg Ser Ser
Gln Ser Leu Leu Asp Ser Asp Gly Lys Thr Tyr Leu Asn
Trp Leu Leu Gln Lys Pro Gly Gln Ser Pro Gln Arg Leu
Ile Tyr Leu Val Ser Lys Arg Asp Ser Gly Val Pro Asp
Arg Phe Ser Gly Ser Gly Ser Gly Thr Asp Phe Thr Leu
Lys Ile Ser Arg Val Glu Ala Glu Asp Val Gly Val Tyr
Tyr Cys Trp Gln Gly Thr His Phe Pro Leu Thr Phe Gly
Gln Gly Thr Lys Leu Glu Ile Lys

SEQ ID NO: 2-[HE ™ ATN-1 VL]
Asp Val Val Met Thr Gln Ser Pro Leu Ser Leu Ser Val
Thr Ile Gly Glu Pro Ala Ser Ile Ser Cys Arg Ser Ser
Gln Ser Leu Leu Asp Ser Asp Gly Lys Thr Tyr Leu Asn
Trp Leu Leu Gln Lys Pro Gly Gln Ser Pro Lys Arg Leu
Ile Tyr Leu Val Ser Lys Arg Asp Ser Gly Val Pro Asp
Arg Phe Ser Gly Ser Gly Ser Gly Thr Asp Phe Thr Leu
Lys Ile Ser Arg Val Glu Ala Glu Asp Val Gly Val Tyr
Tyr Cys Trp Gln Gly Thr His Phe Pro Leu Thr Phe Gly
Gln Gly Thr Lys Leu Glu Ile Lys

SEQ ID NO: 3 [mAh MNPR-101 CDR L1]
Arg Ser Ser Gln Ser Leu Leu Asp Ser Asp Gly Lys Thr
Tyr Leu Asn

SEQ ID NO: 4 [mAh MNPR-101 CDR L2]
Leu Val Ser Lys Arg Asp Ser

SEQ ID NO: 5 mAh [MNPR-101 CDR L3]
Trp Gln Gly Thr His Phe Pro Leu Thr

SEQ ID NO: 6 [LC Signal Sequence]
MSPAQFLFLL VLWIRETNG

SEQ ID NO: 7 [mAh MNPR-101 LC Constant Region Sequence]
RTVAAPSVFI FPPSDEQLKS GTASWCLLN NFYPREAKVQ
WKVDNALQSG NSQESVTEQD SKDSTYSLSS TLTLSKADYE
KHKVYACEVT HQGLSSPVTK SFNRGEC SEQ ID NO: 8 [mAh MNPR-101 low + Moderate Risk-VH]
Glu Val Gln Leu Val Gln Ser Gly Pro Glu Val Lys Lys
Thr Gly Ala Ser Val Lys Ile Ser Cys Lys Ala Ser Gly
Tyr Ser Phe Thr Ser Tyr Tyr Met His Trp Val Arg Gln
Ala His Gly Gln Gly Leu Glu Trp Ile Gly Glu Ile Asn
Pro Tyr Asn Gly Gly Ala Ser Tyr Asn Gln Lys Ile Gln
Gly Arg Ala Thr Phe Thr Val Asp Thr Ser Thr Ser Thr
Ala Tyr Met Glu Phe Ser Ser Leu Arg Ser Glu Asp Thr
Ala Val Tyr Tyr Cys Ala Arg Ser Ile Tyr Gly His Ser
Val Leu Asp Tyr Trp Gly Gln Gly Thr Leu Val Thr Val
Ser Ser SEQ ID NO: 9 [HE ™ ATN-1 VH]
Glu Val Gln Leu Val Gln Ser Gly Pro Glu Val Val Lys
Thr Gly Ala Ser Val Lys Ile Ser Cys Lys Ala Ser Gly
Tyr Ser Phe Thr Ser Tyr Tyr Met His Trp Val Lys Gln
Ala His Gly Gln Gly Leu Glu Trp Ile Gly Glu Ile Asn
Pro Tyr Asn Gly Gly Ala Ser Tyr Asn Gln Lys Ile Lys -continued

| Sequences<br>Sequences for the VL and VH as well as the CL and CH regions of the Fab portion of mAb MNPR-101, and also the low risk sequences of the variable regions of both chains (HE ™ ATN-1) are shown below. |
|---|
| Gly Arg Ala Thr Phe Thr Val Asp Thr Ser Thr Arg Thr<br>Ala Tyr Met Glu Phe Ser Ser Leu Arg Ser Glu Asp Thr<br>Ala Val Tyr Tyr Cys Ala Arg Ser Ile Tyr Gly His Ser<br>Val Leu Asp Tyr Trp Gly Gln Gly Thr Leu Val Thr Val<br>Ser Ser |
| SEQ ID NO: 10 [mAh MNPR-101 CDR H1]<br>Gly Tyr Ser Phe Thr Ser Tyr Tyr Met His |
| SEQ ID NO: 11 [mAh MNPR-101 HC CDR H2]<br>Glu Ile Asn Pro Tyr Asn Gly Gly Ala Ser Tyr Asn Gln<br>Lys Ile Gln Gly |
| SEQ ID NO: 12 [mAh MNPR-101 HC CDR H3]<br>Ser Ile Tyr Gly His Ser Val Leu Asp Tyr |
| SEQ ID NO: 13 [mAb MNPR-101 HC Signal Sequence]<br>MGWIWIFLFL LSGTAGVHS |
| SEQ ID NO: 14 [mAb MNPR-101 HC Constant Region Sequence]<br>ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKRVEP KSCDKTHTCP PCPAPELLGG<br>PSVFLFPPKP KDTLMISRTP EVTCVVVDVS HEDPEVKFNW<br>YVDGVEVHNA KTKPREEQYN STYRVVSVLT VLHQDWLNGK<br>EYKCKVSNKA LPAPIEKTIS KAKGQPREPQ VYTLPPSREE<br>MTKNQVSLTC LVKGFYPSDI AVEWESNGQP ENNYKTTPPV<br>LDSDGSFFLY SKLTVDKSRW QQGNVFSCSV MHEALHNHYT<br>QKSLSLSPGK |

A SalI restriction site was placed in frame and up-stream of the encoded N-terminus of each of the heavy and light chains and a XhoI site was inserted in frame and down-stream from the encoded C-terminus of each chain for insertion of coding nucleic acids into their expression vectors.

MNPR-101 Production

The heavy and light chain polynucleotides of the monoclonal antibody candidate were packaged in a pUC19 plasmid. cDNA inserts encoding the monoclonal antibodies were cloned out and heavy and light chains were inserted into expression vectors.

After confirmation of the sequences, the DHFR-deficient CHO cell line DUX B11 was transfected with light chain and heavy chain containing vectors and a cationic liposome mixture (LIPOFECTAMINE® 2000; Invitrogen Corp., Carlsbad, CA). Forty-eight hours after transfection, cells were subcloned in 96 well dishes using a purine-free growth medium in the presence of geneticin (G418) and 20 nM methotrexate (MTX).

After selection, all subclones were screened using a hIgG Bethyl ELISA kit. Three vials were frozen down for each of the 12 best subclones. The top 6 best producing subclones were then transferred to a medium supplemented with increasing amounts of methotrexate (MTX), an inhibitor of DHFR. MTX concentrations were sequentially increased from 20 to 1,000 nM during the selection process and then to 1,500 nM MTX. The MTX-resistant clones that grew out were screened by ELISA. After a first series of amplification, the two highest expressing population subclones were obtained in medium containing 1,000 nM MTX. These two clones were amplified up to 1,500 nM MTX before being subcloned at 1,000 nM and 1,500 nM MTX. These subclones are currently being expanded to 6 well plates and will be screened by ELISA in the next few days. The top 2-3 best subclones will be then expanded for the production of a Research Cell Bank after adaptation to serum free medium.

Results

The ligand-binding kinetics of mouse mAb ATN-658 and the above discussed Human Engineered™ ATN-658 antibodies were measured once. The sensorgram results of individual assays indicated that all of the transiently-expressed antibodies displayed a similar affinity with mAb ATN-658 as well as among themselves. Results for the four combinations of two VL and two VH chains are shown below in Table 3.

TABLE 3

| Antibody Variant | ka | kd | KD (pM) |
|---|---|---|---|
| ATN-658 | 3.7e5 | 1.4e−4 | 380 |
| HE ™ ATN-1 | 8.6e5 | 2.4e−4 | 280 |
| HE ™ ATN-2 | 6.8e5 | 2.6e−4 | 380 |
| HE ™ ATN-3 | 9.5e5 | 2.7e−4 | 280 |
| HE ™ ATN-4 | 7.0e5 | 2.7e−4 | 390 |

Antibody HE ™ ATN-4 was renamed MNPR-101.

Another aspect of the invention is a targeted pro-radiopharmaceutical construct depicted in Formula III in which the chelator is chemically bonded to the mAb MNPR-101 humanized monoclonal antibody, where M, and "g" are as before described.

III

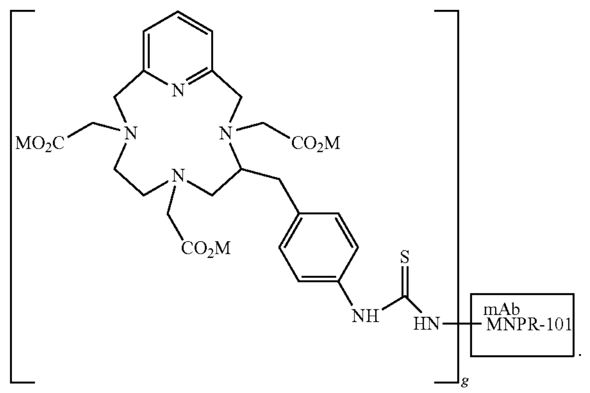

A targeted pro-radiopharmaceutical construct of Formula III is a non-radioactive chemical that can travel in commerce without fear of the dangers of shipping a radioactive entity. Once at or near the site of usage, a targeted pro-radiopharmaceutical construct of Formula III can be dissolved or dispersed in an appropriate medium in which a trivalent radioactive isotope ion, $Q^{+3}$, such as a $^{225}Ac^{+3}$ ion can be added or is already present to form the corresponding targeted radiopharmaceutical of Formula I.

The word "pro-radiopharmaceutical" is used herein to mean that the entity is not itself radioactive and does not have the bioactivity of a radiopharmaceutical. However, upon chelating a trivalent radioactive isotope ion, $Q^{+3}$, becomes a bioactive radiopharmaceutical.

An appropriate medium for forming a contemplated targeted radiopharmaceutical is an aqueous medium such as are discussed below to form a pharmaceutical composition. A targeted radiopharmaceutical so formed is typically separated from unchelated radioisotopes prior to administration to a mammalian host as discussed in the Examples hereinafter regarding the synthesis of such compositions and can be isolated if desired. The concentration of targeted radiopharmaceutical can also be adjusted to a desired level for administration, and salts, buffering agents and the like can be admixed at that time to form a contemplated pharmaceutical composition containing an effective amount of the targeted radiopharmaceutical.

Pharmaceutical Compositions

A pharmaceutical composition containing a theranostic effective amount of a contemplated targeted radiopharmaceutical dissolved or dispersed in a pharmaceutically acceptable diluent is utilized in a contemplated treatment method. In one embodiment, a theranostic effective amount is a targeted cell-killing effective amount as the treatment is therapeutic. Such a composition is administered in vivo into in a mammalian host animal to bind to and kill unwanted targeted cells such as cancer cells and aberrant immune cells.

Illustrative unwanted targeted cells include cells associated with undesired cell migration, invasion, proliferation, immune response or angiogenesis. Illustrative of such cells are abberant immune cells and, cancer cells such as those of lung cancer, ovarian cancer, prostate cancer, brain cancer, bladder cancer, head and neck cancer, pancreatic cancer and colon cancer. Treatment of blood cancers such as acute myeloid leukemia that express the CD33 marker, and breast cancers that express the HER2 marker is also contemplated.

An amount of targeted radiopharmaceutical $Q^{+3}$ ion administered to provide a targeted cell-killing effective amount usually varies with the patient and the severity of the disease such as the tumor load in cancer situations. However, about 80 to about 120 kBq/kg body weight every other month (bimonthly, at about 60-day intervals) typically shows positive results. The use of three cycles of about 100 kBq/kg body weight with the same administration regimen was reported to provide positive results using $^{225}$AC-PSMA-617 that utilizes a DOTA-based chelating agent linked to a peptidomimetic targeting species in prostate cancer patients leading to complete remissions in some patients. See, Kratochwil et al., *J Nucl Med* 2016 57(12):1941-1944; Langbein et al., *J Nucl Med* 2019 60:13S-19S; and Eder et al., *Pharmaceuticals* 2022 15:267. Such dosages can be used to provide a basis for dosages for therapeutic treating of other conditions.

For diagnostic purposes, the host is administered a theranostic amount that is a target cell-binding (diagnostic) effective amount of the targeted radiopharmaceutical. The host is thereafter maintained for a time period of about 1 hour to several days, more usually about 1 to about 4 hours, for the radiopharmaceutial to bind to the targeted cells. The maintenance times can depend on several factors such as the decay rate of the trivalent isotope used and the clearance rate of the targeted radiopharmaceutical. The maintained host mammal is thereafter scanned as by a PET scan for positron emissions (PET scan) or by a gamma ray detector (e.g., SPECT scan) to detect and locate the radiation emitted by the target cell-bound targeted radiopharmaceutical, and thereby identify one or more of the following 1) that targeted cells were present in the host, 2) the location in the host body of the targeted cells, 3) the size and possibly 4) the shape of the mass of cells bound by the targeting species.

The diagnostically-effective amount of targeted radiopharmaceutical administered is typically enough radioisotope to provide about 0.5 to about 6 mCi for an adult, and appropriately less for a child. In-111 is typically used at about 111 MBq (3 mCi) to about 222 MBq (6 mCi) for intravenous administration to an average adult (70 kg). Patients can receive Zr-89 at about 0.5 to about 2 mCi by intravenous administration for a whole-body PET scan.

Because a contemplated targeted radiopharmaceutical pharmaceutical composition is intended for parenteral administration as by injection, such a composition should contain an electrolyte, and preferably have approximately physiological osmolality and pH value of the mammalian species intended as the recipient. A preferred concentration of singly charged electrolyte ions in a targeted radiopharmaceutical pharmaceutical composition is about 0.5 to about 1.5% (w/v), more preferably at about 0.8 to about 1.2% (w/v), and most preferably at a concentration of about 0.9% (w/v). The about 0.9% (w/v) concentration is particularly preferred because it corresponds to an approximately isotonic solution for a human. In a further preferred embodiment, the electrolyte in a chemoablative pharmaceutical composition is sodium chloride.

Electrolytes at such levels increase the osmolality of the targeted radiopharmaceutical pharmaceutical composition. Thus, as an alternative to specifying a range of electrolyte concentrations, osmolality can be used to characterize, in part, the electrolyte level of the composition. It is preferred that the osmolality of a composition be greater than about 100 mOsm/kg and less that about 520 mOsm/kg, more preferably that the osmolality of the composition be greater than about 250 mOsm/kg, and most preferably that it be about 300 to about 500 mOsm/kg.

It is preferred that the pH value of the targeted radiopharmaceutical composition be about 4 to about 9, to yield maximum solubility of the targeted radiopharmaceutical in an aqueous vehicle and assure compatibility with biological tissue. A particularly preferred pH value is about 5 to about 8, and more preferably between about 6 to about 7.5.

The pH value of the targeted radiopharmaceutical pharmaceutical composition can be regulated or adjusted by any suitable means known to those of skill in the art. The composition can be buffered or the pH value adjusted by addition of acid or base or the like.

Because a contemplated targeted radiopharmaceutical pharmaceutical composition is intended for parenteral administration route, it is further preferred that it be sterile, such as required for conformance to U.S. Pharmacopeia (USP) <71>, and further that it contains negligible levels of pyrogenic material, such that it conforms to USP <85> (limulus amebocyte lysate assay) or to USP <151> (rabbit pyrogen test), or to substantially equivalent requirements, at a pyrogen or endotoxin level equivalent to not more than (NMT) 10 endotoxin units (EU) per mL. Moreover, the pharmaceutical composition should conform to requirements limiting content of particulate matter as defined in USP <788> (i.e., NMT 3000 particulates greater than 10 microns in size, and NMT 300 particulates greater than 25 microns in size, per container) or substantially equivalent requirements. Each of these references from the USP is incorporated herein by reference.

Illustrative mammalian animal hosts to which a contemplated targeted radiopharmaceutical composition can be administered include a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

A contemplated pharmaceutical composition is usually administered a plurality of times to a mammalian host over a period of weeks, or months. As noted, a usual administration regimen is carried out every other month. Screenings of the host between administrations provides updates from which an attending physician can make determinations concerning further treatments. As noted before, a series of three bimonthly (at about 60-day intervals administrations of a composition of a different Ac-225-containing targeted radiopharmaceutical pharmaceutical at 100 kBq/kg each produced complete remissions in some prostate cancer patients.

Formulation of parenteral compositions is discussed in, for example, Hoover, John E., *Remington's Pharmaceutical Sciences*, Mack Publishing Co., Easton, Pennsylvania; 1975 and Liberman, H. A. and Lachman, L., Eds., *Pharmaceutical Dosage Forms*, Marcel Decker, New York, N.Y., 1980.

For injectable preparations, for example, sterile injectable aqueous suspensions can be formulated according to the known art using a suitable dispersing or wetting compound and suspending materials. The sterile injectable preparation can also be a sterile injectable solution or suspension in a nontoxic parenterally acceptable diluent or solvent, for example, as a solution in 1,3-butanediol. Among the acceptable vehicles and solvents that can be employed are aqueous liquids at ambient temperature such as water, Ringer's solution, and isotonic sodium chloride solution, phosphate-buffered saline. Liquid pharmaceutical compositions include, for example, solutions suitable for parenteral administration. Sterile water solutions of targeted radiopharmaceutical or sterile solution of the targeted radiopharmaceutical in solvents comprising water, ethanol, DMSO or propylene glycol are examples of liquid compositions suitable for parenteral administration.

Sterile solutions can be prepared by dissolving the targeted radiopharmaceutical component in the desired solvent system, and then passing the resulting solution through a membrane filter to sterilize it or, alternatively, by dissolving the sterile compound in a previously sterilized solvent under sterile conditions.

EXAMPLES

Example 1

Two bifunctional chelators were purchased from Macrocyclics, Dallas, TX. The structure of the two are shown below. They will be referred to as DOTA and PCTA.

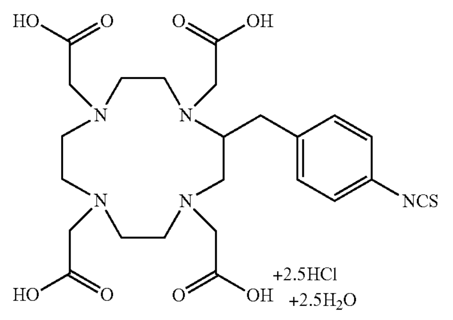

p-SCN-Bn-DOTA

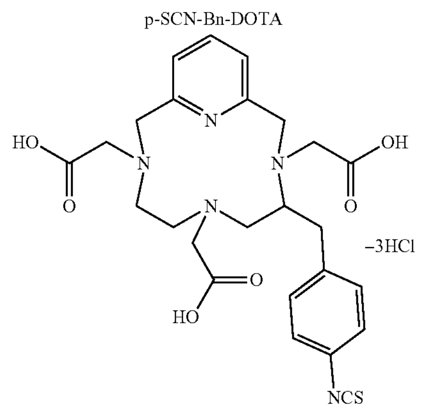

p-SCN-Bn-PCTA

Conjugation reactions with a monoclonal antibody (MNPR-101) were performed in metal-free vials and glassware was acid washed to remove potential metal contamination. Reactions were performed with 2 mg of antibody and increasing molar reactant ratios of bifunctional chelating agents.

Monoclonal antibody (mAb) MNPR-101 is a humanized version of mAb ATN-658 having ATCC Accession Number PTA-8191 of U.S. Pat. No. 8,101,726, and Monopar Therapeutics Inc. The mAb MNPR-101 paratope amino acid residue sequence (CDR; complementarity determining region) is the same as that of ATN-658, whereas the Fc portion is that of a human IgG1 antibody.

For PCTA chelators the molar reaction ratios were 1, 3, 5, 10 and 20. For the DOTA chelators the molar reaction ratios were 3, 10, 25, 50 and 100. The pH of the solutions was adjusted to 9.2 with 1 M $Na_2CO_3$. Reactions were run at 37° C. for 1.5 hours.

Bio-Rad 10DG gravity-fed columns with a 6,000 Dalton molecular weight cut-off were used purify the conjugates. The columns were rinsed with 15 mL of 0.1 M HEPES buffer in 0.1M NaCl. The pH of the buffer was 7.3. The total contents of the reaction vials were introduced to the top of the column and collected in 2 mL tubes. Multiple 0.5 mL elutions with the same buffer were also captured in separate tubes. The UV absorbance at 280 nm of each fraction was measured to determine the fractions containing protein. Typically, protein eluted in 4 fractions that were combined. The protein content of the combined fractions was measured using a PIERCE™ BCA assay kit. The concentrations of the protein conjugates produced was about 1 mg/mL.

Analysis of each conjugate was performed with size exclusion HPLC. The column was from IGM Tosoh (TSKgelG3000SWx1; Tosoh Bioscience LLC, King of Prussia, PA). The mobile phase was phosphate-buffered saline and the flow rate was 1 mL/minute. A UV detector at 280 nm was used. HPLC results showed an early-eluting peak with about an 8-minute retention time consistent with high purity conjugates. The retention time of the conjugates decreased slightly with higher ratios of bifunctional chelators consistent with the addition of chelants to the antibody.

Example 2

Conjugates were prepared by the method of Example 1 but with a chelant to protein molar reaction ratios of 12 and 25. Typical reaction yields are about 30%. Thus, average CAR numbers of about 4 and 8 are expected for the reactions.

Ac-225 was obtained from ORNL (Oak Ridge National Laboratory, Oak Ridge, TN). The reaction vial contained solid Ac-225 which was dissolved using 0.2 M HCl. The same 4 conjugates as described in the previous section were used to prepare Ac-225 chelates. A ratio of 50 μCi of Ac-225 to 50 μg MNPR-101-PCTA chelant conjugate was used such that if there were a 100% yield, the specific activity would be 1 mCi/mg. Reactions were run in 100 μL volumes. That volume included about 4 μL Ac-225 in 0.2M HCl, 60 μL 0.1 M ammonium acetate buffer, and 36 μL MNPR-101-PCTA or -DOTA conjugate. Reactions were incubated at pH 5.8 and 37° C. for 60 minutes.

The radiochemical yield of the reactions was determined by diluting a 50 μL aliquot of reaction to 3 mL in buffer and passing through a 30 kDa Amicon® filter. Small, non-chelated Ac-225 ions pass through the filter, whereas the conjugate is retained by the filter. Samples were counted on a Ge detector after 45 minutes using the first daughter of Ac-225 (Fr-221). In addition, samples were counted using a dose calibrator after overnight (about 18 hours) equilibration of Ac with its daughters. The results of the chelation are shown below.

| | GE Detector (Counts) | | | Dose Calibrator (μCi) | | |
|---|---|---|---|---|---|---|
| Conjugate | Product | Filtrate | Yield (%) | Product | Filtrate | Yield (%) |
| PCTA 12:1 | 14572 | 153 | 99.0 | 12.17 | 0.15 | 98.8% |
| PCTA 25:1 | 12434 | 37 | 99.7% | 11.95 | 0.03 | 99.7% |
| DOTA 12:1 | 2985 | 10758 | 21.7 | 2.72 | 9.88 | 21.6% |
| DOTA 25:1 | 4141 | 9965 | 29.4 | 3.51 | 9.02 | 28.0% |

The table above shows quantitative yields for both the PCTA conjugates whereas the DOTA conjugates have much lower yields and there is a significant difference between the 12:1 and 25:1 conjugates. Surprisingly, even at low CAR numbers, the PCTA conjugates exhibit high yields.

The specific activity of the chelates formed from PCTA was 1,000 μCi/g, whereas the specific activity for the chelates from conjugates prepared from DOTA ranged from about 216 to 284 μCi/g. This head-to-head comparison between DOTA and PCTA shows the superiority of the PCTA chelators compared to DOTA chelators for chelating Ac.

High Performance Liquid Chromatography (HPLC) using a size exclusion column with phosphate-buffered saline as a mobile phase was used to determine the purity of the above samples. The HPLC data gave practically the same results as the filtration method.

Example 3

The MNPR-PCTA conjugate of Example 2 with a chelant to antibody starting reaction ratio of 12:1 was chelated with Ac-225. This would produce specific activity of 1 mCi/mg if the reaction were quantitative. The same chelation reaction was performed with the DOTA conjugate of MNPR-101 using a 25:1 chelant to antibody molar reaction ratio. In addition, bovine serum albumin with no chelants added was used as a negative control.

The total volume of each of the reactions was 150 μL. Each of the reactions was measured for yield using the filtration method of Example 2. The percent of the activity in the retentate was used as the yield of the reaction.

In parallel studies, the above reactions were carried out further containing 35 μL of 0.1M diethylenetriamine pentaacetate (DTPA) and the reactions stood at room temperature for one hour. At this time, the filtration method was again used to determine the yield or purity. The results of both studies are shown in the Table below.

| Test Material | Reaction Yield | | | After DTPA Challenge | | |
|---|---|---|---|---|---|---|
| (CAR) | Product | Filtrate | Yield (%) | Product | Filtrate | Yield (%) |
| MNPR-PCTA(12) | 8013 | 72 | 99.1 | 6746 | 131 | 98.1 |
| BSA | 462 | 12938 | 3.4 | 142 | 10999 | 1.3 |
| MNPR-DOTA(25) | 1150 | 11730 | 8.9 | 706 | 11945 | 5.6 |

MNPR-PCTA(12) had an initial yield of 99.1%. After DTPA challenge, the chelate lost only about 1% of the activity. In contrast, the MNPR-DOTA (25) only had an initial yield of 8.9% and that decreased to 5.6% after the DTPA challenge. In addition, the control BSA only showed 3.4% of the activity associated with the protein (non-specific binding) decreasing to 1.3% after DTPA wash. The data are consistent with PCTA outperforming DOTA in the ability to chelate Ac-225 even at a lower CAR ration. In addition, the lack of binding with naked BSA shows that non-specific binding is not an issue.

Example 4

The conjugate between MNPR-101 (MNPR) and PCTA has been shown to efficiently chelate Ac-225. In a head-to-head comparison, Ac-225 chelated much more efficiently to the PCTA conjugate than with the DOTA conjugate.

Ac-225 was obtained from ORNL. The conjugates used for these reactions were previously prepared and described in Examples 2 and 3, above. Bovine serum albumin (BSA) was used as a negative control protein without any chelators attached to it. MNPR-PCTA(12) refers to the MNPR-101 conjugate made with PCTA with a starting molar reaction ratio of 12:1 PCTA to antibody. MNPR-DOTA(25) refers to the conjugate of MNPR-101 with a starting molar reaction ratio of 25 chelators to antibody.

Reactions were targeted to produce 1 mCi/mg assuming 100% incorporation of the Ac into the antibody. The reactions were run in 150 μL volumes and incubated at pH 5.8 and 37° C. for 60 minutes. Following the reaction, 35 μL aliquots of each reaction were mixed with 35 μL of 1M diethylenetriamine pentaacetate (DTPA) and allowed to stand at room temperature for 1 hour.

The solutions were tested for the percent Ac-225 associated with the protein by filtration as described above as a function of time (1, 24 and 72 hours). The results of the initial study are shown in the table below as the percent Ac-225 associated with the protein as a function of time.

| Test Material | 1 hour in DTPA | 24 hours in DTPA | 72 hours in DTPA |
|---|---|---|---|
| MNPR-PCTA(12) | 99% | 98% | 73% |
| BSA | 3.4% | 1.3% | 3.2% |
| MNPR-DOTA(25) | 8.9% | 5.6% | 6.6% |

The percentage designates the relative amount of activity in the filter compared to the total (filter+filtrate). MNPR-PCTA(12) gave the best results with 99% and 98% attached to the antibody (on the filter) after 1 and 24 hour incubation with DTPA. The purity dropped to 73% after 72 hours. Note that there is no radioprotectant added and Ac-225 gives a high radiation dose to the solution. The fact that the isotope remained associated with the protein shows a high degree of stability.

Both the control (BSA) and MNPR-DOTA(25) have significantly lower percentages of the activity associated with the protein. High resolution gamma spectroscopy analysis of the solutions was consistent with the filtration results in Table 1.

The antibody MNPR-101 conjugated with PCTA with a starting chelator to antibody molar reaction ratio of 12:1 was shown to reproducibly chelate Ac-225 in high yield and high specific activity (1,000 μCi/mg). Incubation of the material in excess DTPA showed a high degree of stability even when the formulation did not contain any radioprotectant. A head-to-head comparison with the same antibody conjugated with DOTA with a starting ratio of 25:1 ligand to protein molar ratio gave much lower yields showing the advantage of PCTA over DOTA for chelating Ac-225. Naked BSA was used as a control showing low amounts of non-specific binding.

Example 5

A targeted radiopharmaceutical containing Ac-225 chelated by PCTA bonded to mAb MNPR-101 as illustrated by Formula I was prepared as described earlier. The starting molar ratio of chelator to antibody was 12 to 1. Fifty μCi of Ac-225 was combined with 50 μg of the MNPR-PCTA conjugate and the pH value adjusted to 5.8 with ammonium acetate for 60 minutes at 37 C. The total volume of the reaction was 100 μL.

A volume of 25 μL of the reaction mixture was analyzed on high performance liquid chromatography using a size exclusion column. The mobile phase was 0.1 M phosphate buffer at pH=7.4 and the flow rate was 1 mL/minute. Detection was by UV absorption at 280 nm and also by radiometric detector.

Evaluation of the UV and radiometric detector showed the radioactivity co-eluting with the protein. A size exclusion column separates chemicals based on size. Because most of the radioactivity from a solution of Ac-225 comes from its radioactive daughters, we would expect radioactive metals that are not attached to the protein to elute at a later time. There was no radioactive signal with retention times consistent with small molecules.

This result is consistent with the MNPR-PCTA conjugate chelating radioactive Ac-225 daughters such as Bi-213. Not to be bound by theory but the excellent binding properties of the PCTA conjugate are believed to be a result of the chelator binding not only Ac-225 but daughters such as Bi-213.

Bismuth ions are very insoluble and could precipitate carrying both bismuth and actinium ions. Prevention of bismuth precipitation by the PCTA chelating functionality can help in the chelation of Ac-225.

Similar size exclusion column studies using DOTA as the chelating agent linked to mAb MNPR-101 show different results. Thus, when DOTA is used, the on-line radiation detector shows very little signal associated with the protein and most of the activity in later-eluting peaks that are indicative of radioactive metals that are not attached to the protein.

Example 6

PCTA conjugates were prepared with humanized mAb MNPR-101 in parallel with two other illustrative mouse monoclonal antibodies: mAb ATN-616 and mAb ATN-292. The chelator to protein molar ratios of 12 and 75 were used to optimize subsequent chelation of Ac-225.

MNPR-101 and ATN-616 were conjugated with PCTA at the molar reaction ratio of 12:1, whereas ATN-292 was conjugated at a 75:1 excess. The pH values of the solutions were adjusted to 9.2 with 1 M $NaH_2CO_3$ and 0.2 M HCl. Reactions were run at 37° C. for 1.5 hours.

The conjugates so formed were purified using Bio-Rad 10DG gravity-fed columns (6,000 Dalton (Da) molecular weight cut-off) in which each conjugate was eluted with 0.1 M ammonium acetate buffer, pH 5.77. Eluted fractions (0.5 mL) were collected in 1.5 mL metal-free tubes and were measured at UV absorbance 280 nm. 3 or 4 fractions were combined, depending on concentration of protein in the eluant, and re-concentrated using Amicon® concentrators (30 kDa). Combined fractions were analyzed using a PIERCE™ BCA Assay Kit (Thermofisher; Final protein concentrations were about 2-3 mg/mL).

Size-exclusion high performance liquid chromatography was utilized to analyze conjugate purity, as previously described, with phosphate-buffered saline solvent and flow rate of 1 mL/minute. HPLC results revealed the expected about 8-minute peaks observed from the naked antibodies and decreased retention time (Rt) of the conjugates consistent with addition of the bifunctional chelator PCTA.

Results suggest that the increase in retention time (ΔRt) observed between the conjugates and respective naked mAb(s) is related to the conjugates' subsequent ability to chelate Ac-225, in that a greater ΔRt correlates to a higher number of chelating agents bonded to the antibody. Differences in retention times from the three conjugates and naked antibodies are shown below.

| Naked Ab | Retention Time (Rt) | Ab Conjugate | Protein Rt | ΔRt |
|---|---|---|---|---|
| MNPR-101 | 7.981 | MNPR-101-PCTA (12:1) | 7.685 | 0.296 |
| ATN-616 | 7.551 | ATN-616-PCTA (12:1) | 7.472 | 0.079 |
| ATN-292 | 8.218 | ATN-292-PCTA (75:1) | 7.689 | 0.529 |

Example 7

A reaction vial containing solid Ac-225 was obtained from ORNL and was dissolved using 0.2 M HCl. The three conjugates from Example 6 were used to prepare Ac-225 chelates. A ratio of 100 μCi of Ac-225 to 100 μg mAb-PCTA chelant conjugate for all reactions was used such that if there were a 100% yield, the specific activity would be 1 mCi/mg. Reactions were run in about 110 μL volumes including approximately 10 μL Ac-225 in 0.2 M HCl, 60 μL 0.1 M ammonium acetate buffer, and 40 μL mAb-PCTA conjugate, dependent upon and normalized against each protein concentration. Reactions were incubated at pH 5.7 and 37° C. for 60 minutes.

25 μL aliquots of each chelation reaction were purified by eluting 0.5 mL fractions on Bio-Rad 10DG gravity-fed columns with 0.1 M ammonium acetate buffer. The Ac-labeled conjugate is expected to elute in 3-4 "peak fractions", which are summed against the activity remaining on the column to determine radiochemical yield. After a minimum of 5 hours (to permit Ac equilibration with its daughters), the fractions and respective columns were measured on the dose calibrator (Capintec, setting #086). Results from each chelations' gravity-fed fractions measured on the dose calibrator are shown in the following tables.

| MNPR-101-PCTA-Ac-225 (12:1) | | | ATN-616-PCTA-Ac-225 (12:1) | | | ATN-292-PCTA-Ac-225 (75:1) | | |
|---|---|---|---|---|---|---|---|---|
| Fraction | μCi | Yield (%) | Fraction | μCi | Yield (%) | Fraction | μCi | Yield (%) |
| 1 | 0.02 | 0.1 | 1 | 0.03 | 0.2 | 1 | 0.09 | 0.4 |
| 2 | 0.05 | 0.2 | 2 | 0 | 0.0 | 2 | 0.11 | 0.5 |
| 3 | 0.07 | 0.3 | 3 | 0.01 | 0.1 | 3 | 0.09 | 0.4 |
| 4 | 2.3 | **11.1** | 4 | 0.76 | **3.9** | 4 | 1.66 | **1.7** |
| 5 | 7.4 | **35.7** | 5 | 6.59 | **34.1** | 5 | 7.59 | **37.1** |
| 6 | 5.08 | **24.5** | 6 | 5.05 | **26.1** | 6 | 5.4 | **26.4** |
| 7 | 1.92 | **9.3** | 7 | 2.5 | **12.9** | 7 | 1.97 | **9.6** |
| 8 | 0.45 | 2.2 | 8 | 0.43 | 2.2 | 8 | 0.48 | 2.3 |
| 9 | 0.18 | 0.9 | 9 | 0.13 | 0.7 | 9 | 0.2 | 1.0 |
| 10 | 0.23 | 1.1 | 10 | 0.12 | 0.6 | 10 | 0.1 | 0.5 |
| 11 | 0.07 | 0.3 | 11 | 0.03 | 0.2 | 11 | 0.08 | 0.4 |
| 12 | 0.13 | 0.6 | 12 | 0.06 | 0.3 | 12 | 0.05 | 0.2 |
| 13 | 0.14 | 0.7 | 13 | 0.05 | 0.3 | 13 | 0.08 | 0.4 |
| 14 | 0.09 | 0.4 | 14 | 0.05 | 0.3 | 14 | 0.1 | 0.5 |
| 15 | 0.05 | 0.2 | 15 | 0 | 0.0 | 15 | 0.11 | 0.5 |
| Column | 2.55 | 12.3 | Column | 4 | 18.3 | Column | 2 | 11.5 |
| Total | 21 | | Total | 19 | | Total | 20 | |
| Peak Yield: 80.6% | | | Peak Yield: 77.0% | | | Peak Yield: 75.5% | | |

Peak fractions from each reaction were measured at time points 24 hours and 48 hours post-purification to determine the chelants' ability to retain Ac-225 daughter isotopes. Peak activity increasing as a function of time provides evidence that the chelants did not effectively control the daughter isotopes. However, if activity decreased at a rate consistent with Ac-225 degradation, evidence suggests that the chelants were able to retain Ac-225 and its daughters. Results observed in the tables below provide evidence of the three chelating systems effectively controlling Ac-225 daughters, as each peak activity does not exhibit a radioactivity increase as a function of time.

| ATN-616-PCTA - Ac-225 (12:1) | | | |
|---|---|---|---|
| Fraction | μCi | 24 hr (μCi) | 48 hr (μCi) |
| 5 | 6.59 | NT* | 6.25 |
| 6 | 5.05 | NT* | 5.02 |
| 7 | 2.5 | NT* | 2.43 |

*NT = Not Tested

| MNPR-101-PCTA - Ac-225 (12:1) | | | |
|---|---|---|---|
| Fraction | μCi | 24 hr (μCi) | 48 hr (μCi) |
| 5 | 7.4 | 7.4 | 6.93 |
| 6 | 5.08 | 5.05 | 4.79 |
| 7 | 1.92 | 1.78 | 1.78 |

| ATN-292-PCTA - Ac-225 (75:1) | | | |
|---|---|---|---|
| Fraction | μCi | 24 hr (μCi) | 48 hr (μCi) |
| 5 | 7.59 | 7.49 | 7.1 |
| 6 | 5.4 | 5.25 | 4.97 |
| 7 | 1.97 | 1.87 | 1.79 |

Example 8

20 μL samples of each chelation reaction were analyzed via HPLC using an isocratic method (1×PBS solvent, pH 7.4) with detection method via UV absorption at 280 nm and radiometric detector. 1 mL fractions were collected per minute and permitted to equilibrate (>5 hours) then were measured on a NaI detector with a wide window.

As observed in Example 5, HPLC results showed the radioactivity co-eluting with the proteins from the three reactions. There was no radioactive signal with a retention time consistent with a small molecule, further supporting the inference that the PCTA chelator binds Ac-225 and its daughters. The results of each reaction yield are shown in the table below:

| NaI Detector, Counts Per Minute | |
|---|---|
| Test Article | Reaction Yield (%) |
| MNPR 101-PCTA - Ac-225 | 96.2% |
| ATN-616-PCTA - Ac-225 | 92.7% |
| ATN-292-PCTA - Ac-225 | 97.8% |

Although the Peak Yields of the three reactions when analyzed by the dose calibrator show 80.6%, 77.0%, and 75.5%, respectively, as described in Example 7, these same reactions show Reaction Yields of 96.2%, 92.7%, and 97.8%, respectively, when analyzed using HPLC purification and NaI detection. This variance is understood to stem from a lack of the ability to measure activity remaining on the size-exclusion column, thus observing the more conservative yields from the Bio-Rad gravity-fed columns and dose calibrator values.

The methods and results described suggest the bifunctional chelator in question, PCTA, shows remarkable ability to bind Ac-225 not only with humanized mAb MNPR-101, but with other antibodies as well, such as the two mouse monoclonal antibodies mAb ATN-616 and mAb ATN-292, and to retain daughter decay products such as Bi-213.

Example 10

An initial study of the chelation characteristics and stability of In-111 using a contemplated PCTA-MNPR-101 chelator-targeting species. Thus, PCTA-MNPR-101 (produced at 12:1) freshly prepared in an aqueous solution at a pH value of 9.2 (1M $NaHCO_3$ and HCl) that contained 4.0 mg/mL by protein analysis was incubated for 1.5 hours at 37° C. The conjugate (220.0 μL MNPR-101-PCTA) was purified by passage through a PD10 column with elution using 0.1M ammonium acetate. Samples containing the conjugate were collected and concentrated using a 30 kDa Amicon® concentrator (4000 rpm for 20 minutes).

Three aqueous chelation reactions were set up, each with activity of about 200 μCi for a target specific activity of 10 mCi/mg. Each was mixed with In-111 chloride obtained from BWXT Medical, Ottawa, ON, Canada. All reactions were stored at 4° C. and assayed for stability after 24, 48 and 72 hours.

Stability in this context is the maintenance of radioactive ion chelation over time. Stability was determined by gravity fed SEC column (PD10 6,000 Dalton cut off), HPLC and TLC for comparison.

Three aqueous chelation reactions were set up, each with activity of about 200 μCi for a target specific activity of 10 mCi/mg. These were as follows:

1) Incubated at 37° C. for 30 minutes. Stored at 4° C. for 72 hours.

2) Incubated at room temperature for 30 minutes. Stored at 4° C. for 24 hours.

3) Incubated at room temperature for 1.5 hours. Stored at 4° C. for 48 hours.

The results of this initial study are shown in the Table below.

| Reaction | Reaction Conditions | Initial TLC (AVG %) | Stability (Hours) | PD10 column (%) | HPLC (%) | Final TLC (Avg %) |
|---|---|---|---|---|---|---|
| 1 | 37°, 30 min | 90.9 | 72 | 65.3 | 87.7 | 94.6 |
| 2 | RT, 30 min | 93.1 | 24 | 84.6 | 83.5 | 87.3 |
| 3 | RT, 1.5 Hr | 90.3 | 48 | 66.1 | 84.5 | 87.3 |

The results of this initial study showed that relatively high yields of chelation were obtained at 10 mCi/mg targeted specific activity. Conditions could likely be optimized to increase yields. Each of the three different analytical methods showed that a chelate was formed. Given that the half-life of Indium-111 is about 2.8 days, reasonable chelated In-111 stability was observed.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. A targeted radiopharmaceutical that has the chemical Formula I, below,

I

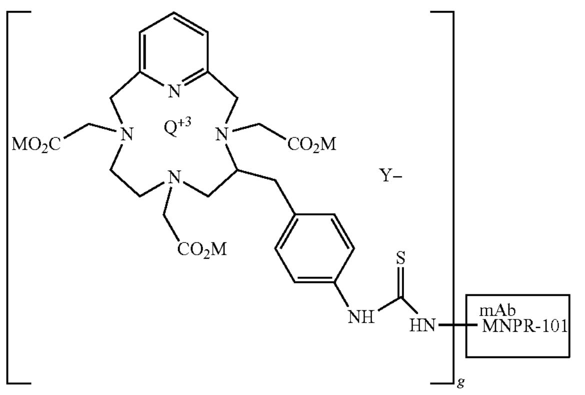

wherein $Q+^3$ is a trivalent radioactive isotope ion;

M is a proton (H+), an ammonium ion or an alkali metal ion;

"g" is a number whose average value is 1 to about 12 that indicates the average number of chelated PCTA-chelated trivalent radioactive ions per each molecule of mAb MNPR-101 or a paratope-containing portion thereof;

the boxed mAb MNPR-101 represents a chemically-bonded monoclonal IgG1 kappa light chain subgroup 2 (VK2) type antibody or antigen-binding fragment thereof, whose kappa chain variable region (VL) comprises CDR L1, CDR L2 and CDR L3 that have the respective sequential combination of amino acid residue sequences, respectively, of SEQ ID NO:3, SEQ ID NO:4 and SEQ ID NO:5; and whose heavy chain variable region (VH) comprises CDR H1, CDR H2 and CDR H3 that have the respective sequential type 1 combination of amino acid residue sequences of SEQ ID NO: 10, SEQ ID NO: 11 and SEQ ID NO: 12; and $Y^-$ is an optional anion present in an amount needed to balance the ionic charge.

2. The targeted radiopharmaceutical according to claim 1, wherein said $V_L$ has the amino acid residue sequence of SEQ ID NO: 1 or SEQ ID NO: 2.

3. The targeted radiopharmaceutical according to claim 1, wherein the kappa chain constant region ($L_c$) has the amino acid residue sequence of SEQ ID NO: 7.

4. The targeted radiopharmaceutical according to claim 1, wherein said heavy chain variable (VH) region has the amino acid residue sequence of SEQ ID NO: 8 or SEQ ID NO: 9.

5. The targeted radiopharmaceutical according to claim 1, wherein the heavy chain type 1 constant region (CH1, CH2 and CH3 domains together) has the amino acid residue sequence of SEQ ID NO: 14.

6. A pharmaceutical composition that comprises a theranostic effective amount of a targeted radiopharmaceutical according to claim 1 dissolved or dispersed in a pharmaceutically acceptable diluent.

7. The pharmaceutical composition according to claim 6, wherein said pharmaceutically acceptable diluent is an aqueous liquid at ambient temperature and is adapted for parenteral administration.

8. The pharmaceutical composition according to claim 7, wherein said composition is isotonic to the blood of the intended mammalian species host recipient.

9. The pharmaceutical composition according to claim 8, wherein said intended mammalian species host recipient is a human.

10. The pharmaceutical composition according to claim 8, wherein said antibody or antigen-binding fragment thereof is bonded to an average of about 3 to about 12.

11. The targeted radiopharmaceutical according to claim 1, wherein $Q+^3$ is an Ac-225, Bi-212, Bi-213, Zr-89 or In-111 ion.

12. A method for treating a mammalian host having a disease, disorder or condition characterized by tumor growth and/or tumor metastasis comprising administering to said host a pharmaceutical composition of claim 6 wherein said theranostic effective amount is a targeted cell-killing effective amount of said targeted radiopharmaceutical.

13. The method according to claim 12, wherein the disease, disorder or condition is cancer.

14. The method according to claim 13, wherein said cancer is selected from the group consisting of one or more of lung cancer, ovarian cancer, prostate cancer, brain cancer, bladder cancer, head and neck cancer, pancreatic cancer or colon cancer.

15. The method according to claim 12, wherein said mammalian host is a human.

16. The method according to claim 12, wherein said administration is repeated.

17. The method according to claim 15, wherein said targeted radiopharmaceutical is administered in an amount sufficient to provide about 80 to about 120 kBq/kg body weight to said mammalian host.

18. The method according to claim 17, wherein said administration is repeated.

19. The method according to claim 18, wherein said administration is repeated at about 60-day intervals.

20. A method for assaying a mammalian host having a disease, disorder or condition characterized by undesired angiogenesis, tumor growth and/or tumor metastasis comprising a) administering to said host a pharmaceutical composition of claim 6 wherein said theranostic amount is a diagnostically effective amount of said targeted radiopharmaceutical;

b) maintaining said host for a time period of about 1 hour to several days for the radiopharmaceutical to bind to the targeted cells; and c) scanning the maintained host to detect and locate the radiation emitted by the target cell-bound targeted radiopharmaceutical.

21. The method according to claim 20, wherein the disease, disorder or condition is cancer.

22. The method according to claim 21, wherein said cancer is selected from the group consisting of one or more of lung cancer, ovarian cancer, prostate cancer, brain cancer, bladder cancer, head and neck cancer, pancreatic cancer or colon cancer.

23. The method according to claim 22, wherein said mammalian host is a human.

24. The method according to claim 20, wherein said administration is repeated.

25. The method according to claim 23, wherein said targeted radiopharmaceutical is administered in an amount of about 0.5 to about 6.0 mCi to said human.

26. A targeted pro-radiopharmaceutical PCTA chelate construct depicted in Formula III in which the chelator is chemically bonded to the mAb MNPR-101 humanized monoclonal antibody,

III

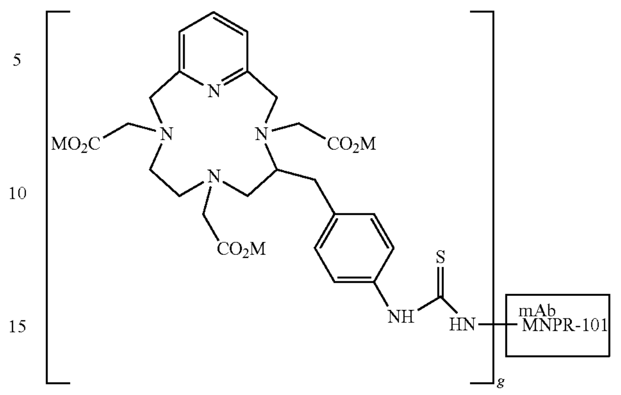

wherein M is a proton (H+), an ammonium ion or an alkali metal ion;

"g" is a number whose average value is about 1 to about 12 that indicates the average number of PCTA-chelate molecules per each molecule of mAb MNPR-101 or a paratope-containing portion thereof;

the boxed mAb MNPR-101 represents a chemically-bonded monoclonal IgG1 kappa light chain subgroup 2 (VK2) type antibody or antigen-binding fragment thereof, wherein the VK2 antibody comprises a variable region ($V_L$) having the amino acid residue sequence of SEQ ID NO: 1 and a kappa chain constant region ($L_c$) having the amino acid residue sequence of SEQ ID NO: 7; and whose heavy chain variable region (VH) has the amino acid residue sequence of SEQ ID NO: 8 and heavy chain type 1 constant region (CH1, CH2 and CH3 domains together) has the amino acid residue sequence of SEQ ID NO: 1.

* * * * *

```
SEQUENCE LISTING

<160> NUMBER OF SEQ ID NOS: 14

<210> SEQ ID NO 1
<211> LENGTH: 112
<212> TYPE: PRT
<213> ORGANISM: Artificial Sequence
<220> FEATURE:
<223> OTHER INFORMATION: Synthetic: mAb MNPR-101 VL

<400> SEQUENCE: 1

Asp Val Val Met Thr Gln Ser Pro Leu Ser Leu Ser Val Thr Ile Gly
1               5                   10                  15

Glu Pro Ala Ser Ile Ser Cys Arg Ser Ser Gln Ser Leu Leu Asp Ser
            20                  25                  30
```

```
Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Leu Thr Phe Gly Gln Gly Thr Lys Leu Glu Ile Lys
            100                 105                 110


<210> SEQ ID NO 2
<211> LENGTH: 112
<212> TYPE: PRT
<213> ORGANISM: Artificial Sequence
<220> FEATURE:
<223> OTHER INFORMATION: Synthetic: HE(TM) ATN-1 VL

<400> SEQUENCE: 2

Asp Val Val Met Thr Gln Ser Pro Leu Ser Leu Ser Val Thr Ile Gly
1               5                   10                  15

Glu Pro Ala Ser Ile Ser Cys Arg Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Lys Arg Leu Ile Tyr Leu Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Leu Thr Phe Gly Gln Gly Thr Lys Leu Glu Ile Lys
            100                 105                 110


<210> SEQ ID NO 3
<211> LENGTH: 16
<212> TYPE: PRT
<213> ORGANISM: Artificial Sequence
<220> FEATURE:
<223> OTHER INFORMATION: Synthetic: mAb MNPR-101 CDR L1

<400> SEQUENCE: 3

Arg Ser Ser Gln Ser Leu Leu Asp Ser Asp Gly Lys Thr Tyr Leu Asn
1               5                   10                  15


<210> SEQ ID NO 4
<211> LENGTH: 7
<212> TYPE: PRT
<213> ORGANISM: Artificial Sequence
<220> FEATURE:
<223> OTHER INFORMATION: Synthetic: mAb MNPR-101 CDR L2

<400> SEQUENCE: 4

Leu Val Ser Lys Arg Asp Ser
1               5


<210> SEQ ID NO 5
<211> LENGTH: 9
<212> TYPE: PRT
<213> ORGANISM: Artificial Sequence
<220> FEATURE:
```

```
<223> OTHER INFORMATION: Synthetic: mAb MNPR-101 CDR L3

<400> SEQUENCE: 5

Trp Gln Gly Thr His Phe Pro Leu Thr
1               5


<210> SEQ ID NO 6
<211> LENGTH: 19
<212> TYPE: PRT
<213> ORGANISM: Artificial Sequence
<220> FEATURE:
<223> OTHER INFORMATION: Synthetic: LC Signal Sequence

<400> SEQUENCE: 6

Met Ser Pro Ala Gln Phe Leu Phe Leu Leu Val Leu Trp Ile Arg Glu
1               5                   10                  15

Thr Asn Gly


<210> SEQ ID NO 7
<211> LENGTH: 107
<212> TYPE: PRT
<213> ORGANISM: Artificial Sequence
<220> FEATURE:
<223> OTHER INFORMATION: Synthetic: mAb MNPR-101 LC Constant Region
      Sequence

<400> SEQUENCE: 7

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 8
<211> LENGTH: 119
<212> TYPE: PRT
<213> ORGANISM: Artificial Sequence
<220> FEATURE:
<223> OTHER INFORMATION: Synthetic: mAb MNPR-101 low + Moderate Risk-VH

<400> SEQUENCE: 8

Glu Val Gln Leu Val Gln Ser Gly Pro Glu Val Lys Lys Thr Gly Ala
1               5                   10                  15

Ser Val Lys Ile Ser Cys Lys Ala Ser Gly Tyr Ser Phe Thr Ser Tyr
            20                  25                  30

Tyr Met His Trp Val Arg Gln Ala His Gly Gln Gly Leu Glu Trp Ile
        35                  40                  45

Gly Glu Ile Asn Pro Tyr Asn Gly Gly Ala Ser Tyr Asn Gln Lys Ile
    50                  55                  60

Gln Gly Arg Ala Thr Phe Thr Val Asp Thr Ser Thr Ser Thr Ala Tyr
65                  70                  75                  80
```

-continued

```
Met Glu Phe Ser Ser Leu Arg Ser Glu Asp Thr Ala Val Tyr Tyr Cys
                85                  90                  95

Ala Arg Ser Ile Tyr Gly His Ser Val Leu Asp Tyr Trp Gly Gln Gly
            100                 105                 110

Thr Leu Val Thr Val Ser Ser
        115


<210> SEQ ID NO 9
<211> LENGTH: 119
<212> TYPE: PRT
<213> ORGANISM: Artificial Sequence
<220> FEATURE:
<223> OTHER INFORMATION: Synthetic: HE(TM) ATN-1 VH

<400> SEQUENCE: 9

Glu Val Gln Leu Val Gln Ser Gly Pro Glu Val Val Lys Thr Gly Ala
1               5                   10                  15

Ser Val Lys Ile Ser Cys Lys Ala Ser Gly Tyr Ser Phe Thr Ser Tyr
            20                  25                  30

Tyr Met His Trp Val Lys Gln Ala His Gly Gln Gly Leu Glu Trp Ile
        35                  40                  45

Gly Glu Ile Asn Pro Tyr Asn Gly Gly Ala Ser Tyr Asn Gln Lys Ile
    50                  55                  60

Lys Gly Arg Ala Thr Phe Thr Val Asp Thr Ser Thr Arg Thr Ala Tyr
65                  70                  75                  80

Met Glu Phe Ser Ser Leu Arg Ser Glu Asp Thr Ala Val Tyr Tyr Cys
                85                  90                  95

Ala Arg Ser Ile Tyr Gly His Ser Val Leu Asp Tyr Trp Gly Gln Gly
            100                 105                 110

Thr Leu Val Thr Val Ser Ser
        115


<210> SEQ ID NO 10
<211> LENGTH: 10
<212> TYPE: PRT
<213> ORGANISM: Artificial Sequence
<220> FEATURE:
<223> OTHER INFORMATION: Synthetic: mAb MNPR-101 CDR H1

<400> SEQUENCE: 10

Gly Tyr Ser Phe Thr Ser Tyr Tyr Met His
1               5                   10


<210> SEQ ID NO 11
<211> LENGTH: 17
<212> TYPE: PRT
<213> ORGANISM: Artificial Sequence
<220> FEATURE:
<223> OTHER INFORMATION: Synthetic: mAb MNPR-101 HC CDR H2

<400> SEQUENCE: 11

Glu Ile Asn Pro Tyr Asn Gly Gly Ala Ser Tyr Asn Gln Lys Ile Gln
1               5                   10                  15

Gly


<210> SEQ ID NO 12
<211> LENGTH: 10
<212> TYPE: PRT
<213> ORGANISM: Artificial Sequence
<220> FEATURE:
<223> OTHER INFORMATION: Synthetic: mAb MNPR-101 HC CDR H3
```

<400> SEQUENCE: 12

```
Ser Ile Tyr Gly His Ser Val Leu Asp Tyr
1               5                   10
```

<210> SEQ ID NO 13
<211> LENGTH: 19
<212> TYPE: PRT
<213> ORGANISM: Artificial Sequence
<220> FEATURE:
<223> OTHER INFORMATION: Synthetic: mAb MNPR-101 HC Signal Sequence

<400> SEQUENCE: 13

```
Met Gly Trp Ile Trp Ile Phe Leu Phe Leu Leu Ser Gly Thr Ala Gly
1               5                   10                  15

Val His Ser
```

<210> SEQ ID NO 14
<211> LENGTH: 330
<212> TYPE: PRT
<213> ORGANISM: Artificial Sequence
<220> FEATURE:
<223> OTHER INFORMATION: Synthetic: mAb MNPR-101 HC Constant Region Sequence

<400> SEQUENCE: 14

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

-continued

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```